United States Patent
Thorens

(10) Patent No.: US 11,116,920 B2
(45) Date of Patent: Sep. 14, 2021

(54) AEROSOL-GENERATING ARTICLE WITH LIQUID-IMPERVIOUS WRAPPER, AEROSOL-GENERATING SYSTEM, AND A METHOD OF USING THE AEROSOL-GENERATING ARTICLE

(71) Applicant: Altria Client Services LLC, Richmond, VA (US)

(72) Inventor: Michel Thorens, Moudon (CH)

(73) Assignee: Altria Client Services LLC, Richmond, VA (US)

( * ) Notice: Subject to any disclaimer, the term of this patent is extended or adjusted under 35 U.S.C. 154(b) by 189 days.

(21) Appl. No.: 15/711,237

(22) Filed: Sep. 21, 2017

(65) Prior Publication Data
US 2018/0015237 A1 Jan. 18, 2018

Related U.S. Application Data

(63) Continuation of application No. PCT/EP2017/063061, filed on May 30, 2017.

(30) Foreign Application Priority Data

May 31, 2016 (EP) .................................... 16172262
May 31, 2016 (EP) .................................... 16172263

(Continued)

(51) Int. Cl.
*A61M 15/06* (2006.01)
*A61M 11/04* (2006.01)
(Continued)

(52) U.S. Cl.
CPC .............. *A61M 15/06* (2013.01); *A24D 1/20* (2020.01); *A24F 40/30* (2020.01); *A24F 40/40* (2020.01);
(Continued)

(58) Field of Classification Search
CPC .............. A61M 15/06; A61M 15/0028; A61M 15/003; A61M 15/0003; A61M 11/041;
(Continued)

(56) References Cited

U.S. PATENT DOCUMENTS 3,502,084 A * 3/1970 Carty ..................... A24D 3/061
131/337
5,369,723 A 11/1994 Counts et al.
(Continued)

FOREIGN PATENT DOCUMENTS

CN 101500443 A 8/2009
CN 103929988 A 7/2014
(Continued)

OTHER PUBLICATIONS

International Search Report and Written Opinion dated Aug. 11, 2017, for related PCT Application No. PCT/EP2017/063061.
(Continued)

*Primary Examiner* — Joseph D. Boecker
*Assistant Examiner* — Thomas W Greig
(74) *Attorney, Agent, or Firm* — Harness, Dickey & Pierce, P.L.C.

(57) ABSTRACT

The aerosol-generating article include a plurality of elements coaxially aligned and assembled within a wrapper, the article having an outlet end and a distal end upstream from the outlet end. The article includes a liquid aerosol-forming substrate, and a liquid retention medium for retaining the liquid aerosol-forming substrate. The wrapper is formed from a sheet of liquid-impervious material, the liquid retention medium being in a first element of the plurality of elements.

20 Claims, 6 Drawing Sheets

(30) Foreign Application Priority Data

May 31, 2016 (EP) .................................... 16172265
May 31, 2016 (EP) .................................... 16172287

(51) Int. Cl.

| | |
|---|---|
| *A61M 15/00* | (2006.01) |
| *A24F 40/42* | (2020.01) |
| *A24D 1/20* | (2020.01) |
| *A24F 40/30* | (2020.01) |
| *A24F 40/40* | (2020.01) |
| *A61M 11/00* | (2006.01) |
| *H05B 6/10* | (2006.01) |
| *A24F 40/10* | (2020.01) |
| *A24D 3/17* | (2020.01) |
| *A24F 40/20* | (2020.01) |
| *A24D 1/02* | (2006.01) |
| *B05B 7/24* | (2006.01) |

(52) U.S. Cl.
CPC ........... *A24F 40/42* (2020.01); *A61M 11/003* (2014.02); *A61M 11/042* (2014.02); *A61M 15/003* (2014.02); *H05B 6/108* (2013.01); *A24D 1/02* (2013.01); *A24D 3/17* (2020.01); *A24F 40/10* (2020.01); *A24F 40/20* (2020.01); *A61M 15/0003* (2014.02); *A61M 15/0021* (2014.02); *A61M 15/0035* (2014.02); *A61M 15/0066* (2014.02); *A61M 2205/0211* (2013.01); *A61M 2205/3606* (2013.01); *A61M 2205/368* (2013.01); *A61M 2205/3646* (2013.01); *A61M 2205/7545* (2013.01); *A61M 2205/8206* (2013.01); *B05B 7/2402* (2013.01)

(58) Field of Classification Search
CPC .... A61M 11/042; A61M 11/08; A24F 47/008; A24D 3/061; A42F 47/008
See application file for complete search history.

(56) References Cited

U.S. PATENT DOCUMENTS

| | | | |
|---|---|---|---|
| 5,408,574 A | 4/1995 | Deevi et al. | |
| 6,164,287 A | 12/2000 | White | |
| 10,178,878 B2* | 1/2019 | Camus | A24D 1/02 |
| 10,499,690 B2 | 12/2019 | Thorens | |
| 2008/0092912 A1 | 4/2008 | Robinson et al. | |
| 2011/0005535 A1 | 1/2011 | Xiu | |
| 2012/0042885 A1* | 2/2012 | Stone | A24B 15/165 |
| | | | 131/194 |
| 2014/0202479 A1* | 7/2014 | Nicholls | A24D 3/048 |
| | | | 131/337 |
| 2014/0209112 A1* | 7/2014 | Awty | A24D 3/061 |
| | | | 131/335 |
| 2014/0373856 A1* | 12/2014 | Zuber | A24D 1/00 |
| | | | 131/328 |
| 2015/0027477 A1* | 1/2015 | Yoshino | A24D 3/04 |
| | | | 131/337 |
| 2016/0029694 A1 | 2/2016 | Clements et al. | |
| 2016/0206003 A1 | 7/2016 | Yamada et al. | |
| 2016/0338402 A1* | 11/2016 | Buehler | B23K 26/362 |
| 2017/0095003 A1 | 4/2017 | Mironov | |
| 2017/0340015 A1 | 11/2017 | Thorens | |
| 2017/0340016 A1 | 11/2017 | Thorens | |
| 2017/0340017 A1 | 11/2017 | Thorens | |
| 2017/0340018 A1 | 11/2017 | Thorens | |
| 2018/0007972 A1 | 1/2018 | Thorens | |
| 2018/0295885 A1 | 10/2018 | Rojo-Calderon et al. | |
| 2019/0098927 A1 | 4/2019 | Mironov | |
| 2020/0060351 A1 | 2/2020 | Thorens | |

FOREIGN PATENT DOCUMENTS

| | | |
|---|---|---|
| CN | 104219972 A | 12/2014 |
| DE | 102014116742 B3 | 7/2015 |
| EP | 2046155 A1 | 4/2009 |
| EP | 2888963 A1 | 7/2015 |
| EP | 3015010 A1 | 5/2016 |
| JP | 2008-523934 A | 7/2008 |
| JP | 2010-520742 A | 6/2010 |
| JP | 2015-524260 A | 8/2015 |
| RU | 1837814 A3 | 8/1993 |
| RU | 2297781 C2 | 4/2007 |
| RU | 103062 U1 | 3/2011 |
| RU | 2509516 C2 | 3/2014 |
| WO | WO-2008015441 A1 | 2/2008 |
| WO | WO-2013/102609 A2 | 7/2013 |
| WO | WO-2014140087 A1 | 9/2014 |
| WO | WO-2015/040180 A2 | 3/2015 |
| WO | WO-2015101651 A1 | 7/2015 |
| WO | WO-2015117705 A2 | 8/2015 |
| WO | WO-2015176898 A1 | 11/2015 |
| WO | WO-2016-058904 A1 | 4/2016 |

OTHER PUBLICATIONS

Written Opinion of the International Searching Authority dated May 31, 2016 in related PCT Application No. PCT/EP2017/063061.
European Search Report for European Application No. EP16172262.4 dated Jan. 13, 2017.
European Search Report for European Application No. EP16172265.7 dated Jan. 17, 2017.
European Search Report for European Application No. EP16172263.2 dated Jan. 17, 2017.
European Search Report for European Application No. EP16172287.1 dated Nov. 16, 2016.
U.S. Appl. No. 15/711,261, filed Sep. 21, 2017.
U.S. Appl. No. 15/711,347, filed Sep. 21, 2017.
U.S. Appl. No. 15/711,257, filed Sep. 21, 2017.
Notice of Allowance dated Jul. 24, 2019 in related U.S. Appl. No. 15/711,347.
Office Action and search report dated Dec. 22, 2020, issued in corresponding Chinese Patent Application No. 201780029098.5.
Written Opinion of the International Preliminary Searching Authority dated May 8, 2018, issued in corresponding PCT Application No. PCT/EP2017/063061.
Office Action and search report dated Jun. 22, 2020, issued in corresponding Russian Patent Application No. 2018142136.
Office Action dated Feb. 3, 2021, issued in corresponding U.S. Appl. No. 16/671,930.
Decision to Grant dated Jul. 29, 2020, issued in corresponding Russian Application No. 2018142136/12.
Notice of Allowance dated May 17, 2021 in related U.S. Appl. No. 16/671,930.
Office Action dated May 24, 2021, issued in corresponding Japanese Patent Application No. 2018-557131.

* cited by examiner

AEROSOL-GENERATING ARTICLE WITH LIQUID-IMPERVIOUS WRAPPER, AEROSOL-GENERATING SYSTEM, AND A METHOD OF USING THE AEROSOL-GENERATING ARTICLE

CROSS-REFERENCE TO RELATED APPLICATIONS

This application is a continuation of, and claims priority to, international application no. PCT/EP2017/063061, filed on May 30, 2017, and further claims priority under 35 U.S.C. § 119 to European Patent Application No. 16172262.4, filed on May 31, 2016, European Patent Application No. 16172265.7, filed on May 31, 2016, European Patent Application No. 16172263.2, filed on May 31, 2016, and European Patent Application No. 16172287.1, filed on May 31, 2016, the entire contents of each of which is incorporated herein by reference in their entirety.

BACKGROUND

Field

Example embodiments relate to a consumable aerosol-generating article for use with an aerosol-generating device, an aerosol-generating system, and a method of using the aerosol generating article. The aerosol generating article may include a liquid aerosol-forming substrate, a liquid retention medium, and a liquid-impervious wrapper.

Related Art

There are generally two main categories of heated aerosol-generating systems that may be used to produce an aerosol by heating, rather than by burning an aerosol-forming substrate. One system, which may be described as an e-cigarette system, typically may include a liquid aerosol-forming substrate contained within a cartridge of an atomiser unit. On operation, liquid may be conveyed from the cartridge by a wick, where it may be vaporized by a heating coil. A second system, which may be described as a heated tobacco system, may involve the heating of a solid substrate including modifying tobacco to produce an aerosol.

SUMMARY

At least a first embodiment is directed toward an aerosol-generating article.

In one embodiment, the aerosol-generating article includes, a plurality of elements coaxially aligned and assembled within a wrapper, the article having an outlet end and a distal end upstream from the outlet end; a liquid aerosol-forming substrate; and a liquid retention medium for retaining the liquid aerosol-forming substrate, wherein the wrapper is formed from a sheet of liquid-impervious material, the liquid retention medium being in a first element of the plurality of elements.

In one embodiment, the liquid aerosol-forming substrate is releasably contained within a frangible capsule, the frangible capsule being near the liquid retention medium for retaining the liquid aerosol-forming substrate within the article after its release from the frangible capsule.

In one embodiment, the frangible capsule is in the liquid retention medium.

In one embodiment, the liquid retention medium is in the form of a tube having a lumen, and the frangible capsule is located within the lumen of the tube.

In one embodiment, the liquid retention medium includes an absorbent polymeric material.

In one embodiment, the frangible capsule is configured to be ruptured by application of an external force.

In one embodiment, the frangible capsule is configured to be pierced by a piercing element.

In one embodiment, the aerosol-generating article further includes, a cooling section located downstream from the liquid retention element, the cooling section being a second element of the plurality of elements.

In one embodiment, the liquid aerosol-forming substrate includes between 10 weight percent and 25 weight percent water, an aerosol former, and at least one flavorant.

In one embodiment, the aerosol-generating article further includes, a mouthpiece filter located at the outlet end of the article, the mouthpiece filter being a third element of the plurality of elements.

In one embodiment, the aerosol-generating article further includes, a plug located at the distal end of the article, the article being configured to draw air into the article at or adjacent to the distal end, through the article, and out of the outlet end of the article if a negative pressure is applied at the outlet end.

In one embodiment, the wrapper is one of a sheet of polymeric material, a sheet of treated paper, and a sheet of metallic foil.

At least another example embodiment relates to an aerosol-generating system.

In one embodiment, the aerosol-generating system includes, an aerosol-generating article, the aerosol-generating article including, a plurality of elements coaxially aligned and assembled within a wrapper, the article having an outlet end and a distal end upstream from the outlet end, a liquid aerosol-forming substrate, and a liquid retention medium for retaining the liquid aerosol-forming substrate, the wrapper being formed from a sheet of liquid-impervious material, the liquid retention medium being in a first element of the plurality of elements; and an electrically-operated aerosol-generating device, the electrically-operated aerosol-generating device including a heating element for heating the aerosol-forming substrate to form an aerosol.

At least another example embodiment relates to a method of using an aerosol generating article.

In one embodiment, the method uses an aerosol generating article, where the aerosol-generating article includes a plurality of elements coaxially aligned and assembled within a wrapper, the article having an outlet end and a distal end upstream from the outlet end, a liquid aerosol-forming substrate, and a liquid retention medium for retaining the liquid aerosol-forming substrate, the wrapper being formed from a sheet of liquid-impervious material, the liquid retention medium being in a first element of the plurality of elements, the method including, coupling the heated aerosol-generating article to an electrically-operated aerosol-generating device; activating a heating element of the electrically-operated aerosol-generating device; and drawing air through the heated aerosol-generating article, the liquid aerosol-forming substrate being vaporized by heat energy supplied by the heating element and condensed to form an aerosol entrained in the air.

In one embodiment, the liquid aerosol-forming substrate is contained within a frangible capsule, the method further including the step of, releasing the liquid aerosol-forming substrate from the frangible capsule such that it is retained within the article by the liquid retention medium.

BRIEF DESCRIPTION OF THE DRAWINGS

Features described in relation to one example embodiment may equally be applied to other example embodiments. Example embodiments will now be described, with reference to the accompanying drawings.

DETAILED DESCRIPTION

Figure 1:
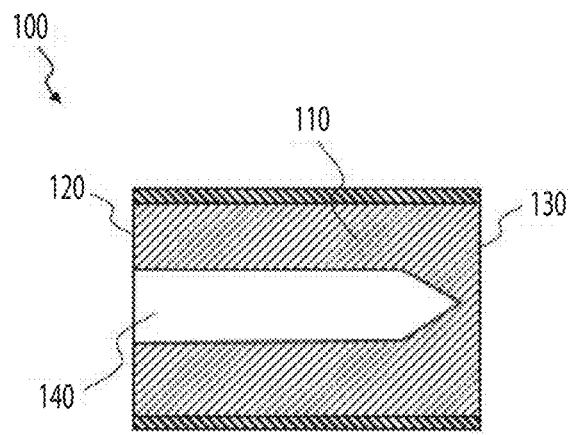
FIG. 1 illustrates a schematic longitudinal cross-section of a heat diffuser of an aerosol-generating system, in accordance with an example embodiment.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

Further, one or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

General Methodology

Of the two main categories of heated aerosol-generating system (highlighted above), the e-cigarette system may require direct heating of the liquid substrate with a heating coil, which may risk overheating of the liquid, particularly if the cartridge may be near empty. Additionally, a typical e-cigarette system may be used by multiple adult vapers, and therefore may come into contact with many external contaminants. This may provide a potential hygiene issue.

A heated tobacco system using a consumable article containing a solid aerosol-forming substrate may produce a sensorially more acceptable aerosol, and may not have the same hygiene problems associated with e-cigarettes. An adult vaper may however desire a wide variety of flavors that may be possible with a liquid-based heated e-cigarette system.

A type of aerosol-generating system is an electrically operated aerosol-generating system. Handheld electrically operated aerosol-generating systems typically include an aerosol-generating device that has a battery, control electronics and an electric heater for heating an aerosol-generating article designed specifically for use with the aerosol-generating device. The aerosol-generating article includes an aerosol-forming substrate, such as a tobacco rod or a tobacco plug, and the heater that may be contained within the aerosol-generating device may be inserted into or around the aerosol-forming substrate when the aerosol-generating article may be inserted into the aerosol-generating device.

It may be difficult to evenly heat the aerosol-forming substrate with the electric heater. This may lead to some areas of the aerosol-forming substrate being over-heated, and may lead to some areas of the aerosol-forming substrate being under-heated. Both may make it difficult to maintain consistent aerosol characteristics. This may be a particular issue with aerosol-generating articles in which the aerosol-forming substrate may be a liquid aerosol-forming substrate, since depletion of the aerosol-forming substrate may cause one or more parts of the aerosol-generating article to overheat. It therefore may be advantageous to provide means for mitigating the above described problems.

In at least one example embodiment there is provided an electrically operated aerosol-generating system comprising an aerosol-generating article and an electrically operated aerosol-generating device. The aerosol-generating article may include an aerosol-forming substrate, with an outlet end and a distal end upstream from the outlet end. The electrically operated aerosol-generating device may include a housing having a cavity configured to receive the distal end of the aerosol-generating article. The aerosol-generating system may further include an electric heating element and a heat diffuser including a non-combustible porous body for absorbing heat from the electric heating element such that, in use, air may be drawn through the aerosol-generating article from the distal end to the outlet end, and may be heated by the heat absorbed in the porous body.

As used herein, the term "heated aerosol-generating article" may refer to an article comprising an aerosol-generating substrate that, when heated, may release volatile compounds that may form an aerosol. A "heated aerosol-generating article" refers to an article including an aerosol-forming substrate that is intended to be heated, rather than combusted, in order to release volatile compounds that can form an aerosol. The aerosol formed by heating the aerosol-forming substrate may contain fewer known harmful constituents than would be produced by combustion or pyrolytic degradation of the aerosol-forming substrate. In an embodiment, the aerosol-generating article is removably coupled to an aerosol-generating device. The article may be disposable or reusable.

As used herein, the term "aerosol-generating device" is a device that engages or interacts with a heated aerosol-generating article to form an aerosol. The device that interacts with an aerosol-forming substrate may generate an aerosol. An electrically operated aerosol-generating device may be a device including one or more elements used to supply energy from a power supply (e.g., an electrical power supply), in order to heat an aerosol-forming substrate to generate an aerosol. The aerosol-generating device may be an electrically operated aerosol-generating device including a heating structure that is operated by electrical power to heat an aerosol-forming substrate of an aerosol-generating article to generate an aerosol. The heating structure may be a heater for heating air supplied to an aerosol-forming substrate. The heating structure may be an inductor for heating a susceptor, for example to heat air supplied to an aerosol-forming substrate.

An aerosol-generating device may be described as a heated aerosol-generating device, which is an aerosol-generating device including a heating element. The heating element or heater may be used to heat an aerosol-forming substrate of an aerosol-generating article to generate an aerosol, or the solvent-evolving substrate of a cleaning consumable to form a cleaning solvent. An aerosol-generating device may be an electrically heated aerosol-generating device, which may be an aerosol-generating device including a heating element that may be operated by electrical power to heat an aerosol-forming substrate of an aerosol-generating article to generate an aerosol.

The electric heating element may form part of the aerosol-generating article, part of the heat diffuser, part of the aerosol-generating device, or any combination thereof. In an embodiment, the electric heating element forms part of the device.

In an embodiment, the heat diffuser may form part of the aerosol-generating article or the aerosol-generating device. In an embodiment, the heat diffuser is removably coupled to the aerosol-generating device. In an embodiment, the heat diffuser may form part of the aerosol-generating article, or may be an independent element that does not form part of the aerosol-generating article or the aerosol-generating device. The heat diffuser may be removably coupled to the aerosol-generating article and the aerosol-generating device. The device may be configured to removably coupled to the heat diffuser. The cavity of the device may be configured to removably receive the heat diffuser. The electric heating element may be configured to thermally couple with the heat diffuser when the heat diffuser is removably coupled to the aerosol-generating device. The electric heating element may be configured to thermally couple with the heat diffuser when the heat diffuser is received in the cavity of the aerosol-generating device.

In this document, the term 'removably coupled' or 'removably couplable' is used to mean that two or more elements of the system, such as the heat diffuser and the device, or the article and the device, may be coupled and uncoupled from one another without significantly damaging either element. For example, the article may be removed from the device when the aerosol-forming substrate has been consumed. The heat diffuser may be disposable. The heat diffuser may also be reusable.

The heat diffuser may be a removable element of the aerosol-generating system. For example, the heat diffuser may be in the form of a removably coupled and/or couplable element that engage with the aerosol generating device to alter the manner in which the aerosol generating device heats the aerosol generating articles. For example, the aerosol generating device may include an insertable heating element for insertion into a solid aerosol forming substrate of a heated aerosol-generating article. The heating element may contact the solid aerosol-forming substrate and heat it to generate an aerosol. The heat diffuser may be configured to engage with the insertable heating element. The heat diffuser may then be heated by the heating element, and the heated air may pass through the heating element. The heated air may volatilize an aerosol-forming substrate of a heated aerosol-generating article that may be located downstream of the heat diffuser. In this way, the manner in which the aerosol-generating device may heat an aerosol-forming substrate may be changed from direct contact to an indirect heating of air. The same aerosol-generating device may be used to heat different types of aerosol-generating article, thereby providing a greater choice for the adult vaper.

In an embodiment, the system may be configured such that when the heat diffuser is coupled to the aerosol-generating device, the heat diffuser absorbs heat from the electric heating element, and air drawn through the aerosol-generating article from the distal end to the outlet end may be heated by the heat absorbed in the porous body of the heat diffuser. The system may further be configured such that when the heat diffuser may not be coupled to the aerosol-generating device, the aerosol-generating article may absorb heat from the electric heating element.

Advantageously, in use, the heat diffuser may absorb heat from a heating element, and transfer the heat to air that may be drawn through the heat diffuser so that the air may heat the aerosol-forming substrate downstream of the heat diffuser, primarily via a convection heating process. This may provide more even heating of the aerosol-forming substrate, relative to systems in which the aerosol-forming substrate is heated primarily via a conduction heating process provided by the heating element. For example, areas of local high temperature, or "hot spots", may be prevented from occurring in the aerosol-forming substrate that may otherwise be caused by conductive heating. This may be of particular benefit when the heat diffuser is used with aerosol-generating articles in which the aerosol-forming substrate is a liquid aerosol-forming substrate, as it may help to prevent overheating that may otherwise result from depletion of the aerosol-forming substrate. In particular, if the aerosol-forming substrate includes a liquid aerosol-forming substrate held in a liquid retention medium, the heat diffuser may help to reduce or prevent overheating of the aerosol-forming substrate or the liquid retention medium, even when the liquid retention medium is dry.

The heat diffuser may be arranged and configured to heat the air to between about 180 degrees Celsius and 250 degrees Celsius. In an embodiment, the heat diffuser heats the air to between about 200 degrees Celsius and 220 degrees Celsius.

In an embodiment, the system includes a heated aerosol-generating device, at least one heated aerosol-generating article having a liquid aerosol-forming substrate, and at least one heated aerosol-forming substrate having a solid aerosol-forming substrate, for example an aerosol-forming substrate made from homogenized tobacco material. The system may further include a removably couplable heat diffuser for engagement with the aerosol-generating device to change the manner in which the aerosol-generating device provides heat to the aerosol-forming substrate.

The term "porous" includes materials that may be inherently porous, as well as substantially non-porous materials that may be made porous and/or permeable through the provision of a plurality of holes. The porous body may be formed from a plug of a porous material, such as a ceramic or metal foam, for example. Alternatively, the porous body may be formed from a plurality of solid elements between which a plurality of apertures are provided. For example, the porous body may include a bundle of fibres, or a lattice of interconnected filaments. The porous material may have pores of a sufficient size that may allow air to be drawn through the porous body, through the pores. For example, the pores in the porous body may have an average transverse dimension of less than about 3.0 mm, or more preferably less than about 1.0 mm, or most preferably less than about 0.5 mm. Alternatively or in addition, the pores may have an average transverse dimension that may be greater than about 0.01 mm. For example, the pores may have an average transverse dimension that may be between about 0.01 mm and about 3.0 mm, or more preferably between about 0.01 mm and about 1.0 mm, or most preferably between about 0.01 mm and about 0.5 mm.

The term "pores" relates to regions of a porous article that are devoid of material. For example, a transverse area of porous body may include portions of the material forming the body, and portions that may be voids between the portions of material.

The average transverse dimension of the pores may be calculated by taking the average of the smallest transverse dimension of each of the pores. The pore sizes may be substantially constant along the length of the porous body. Alternatively, the pore sizes may vary along the length of the porous body.

The term "transverse dimension" refers to a dimension that is in a direction which may be substantially perpendicular to the longitudinal direction of the heated aerosol-generating article, the electrically operated aerosol-generating device, or the porous body.

The porosity distribution of the porous body may be substantially uniform. That is, the pores within the porous body may be distributed substantially evenly over the transverse area of the porous body. The porosity distribution may differ across the transverse area of the porous body. That is, the local porosity in one or more sub-areas of the transverse area may be greater than the local porosity in one or more other sub-areas of the transverse area. For example, the local porosity in one or more sub-areas of the transverse area may be between 5 percent and 80 percent greater than the local porosity in one or more other sub-areas of the transverse area.

The term "transverse area" relates to an area of the porous body that is in a plane generally perpendicular to the longitudinal dimension of the porous body. For example, the porous body may be a rod and the transverse area may be a cross-section of the rod taken at any length along the rod, or the transverse area may be an end face of the rod.

The term "porosity" refers to the volume fraction of void space in a porous article. As used herein, the term "local porosity" refers to the fraction of pores within a sub-area of the porous body.

By varying the porosity distribution, air flow through the porous body may be altered as desired, for example to provide improved aerosol characteristics. For example, this porosity distribution may be varied according to the air flow characteristics of an aerosol-generating system, or the temperature profile of a heating element, with which the heat diffuser is intended for use.

In an embodiment, the local porosity may be lower towards a center portion of the porous body. With this arrangement, the air flow through the center portion of the porous body is decreased relative to the periphery of the porous body. This may be advantageous depending on the temperature profile of the heating element or on the airflow characteristics of the aerosol-generating system with which the heat diffuser is intended for use. For example, this arrangement may be of particular benefit when used with an internal heating element positioned in use towards a central portion of the heat diffuser, since it may allow for increased heat transfer from the heating element to the porous body.

In an embodiment, the local porosity may be greater towards a center portion of the porous body. This arrangement may enable increased air flow through the center of the porous body and may be advantageous depending on the temperature profile of the heating element or on the airflow characteristics of the aerosol-generating system with which the heat diffuser is intended for use. For example, this arrangement may be of particular benefit when used with an external heating element positioned in use around the periphery of the heat diffuser, since it may allow for increased heat transfer from the heating element to the porous body.

As porous bodies have a high surface-area-to-volume ratio, the heat diffuser may allow quick and efficient heating of air drawn through the porous body. This may allow for homogenous heating of air drawn through the porous body and, consequently, more even heating of an aerosol-forming substrate downstream of the heat diffuser.

In an embodiment, the porous body has a surface area-to-volume ratio of at least 20 to 1, or preferably at least 100 to 1, or more preferably at least 500 to 1. Advantageously, this may provide a compact heat diffuser while allowing for particularly efficient transfer of thermal energy from the heating element to air drawn through the porous body. This may lead to faster, and more homogenous heating of air drawn through the porous body and, consequently, a more even heating of the aerosol-forming substrate downstream of the heat diffuser, relative to porous bodies having a lower surface area to volume ratios.

In an embodiment, the porous body has a high specific surface area. This may be a measure of the total surface area of a body per unit of mass. Advantageously, this may provide a low mass heat diffuser with a large surface area for efficient transfer of thermal energy from the heating element to air drawn through the porous body. For example, the porous body may have a specific surface area of at least 0.01 $m^2$ per gram, or preferably at least 0.05 $m^2$ per gram, or more preferably at least 0.1 $m^2$ per gram, or most preferably at least 0.5 $m^2$ per gram.

The porous body may have an open cell porosity of between about 60 percent to about 90 percent void volume to material volume.

In an embodiment, the porous body may have a low resistance to draw. That is, the porous body may offer a low resistance to the passage of air through the heat diffuser. In such examples, the porous body may not substantially affect the resistance to draw of an aerosol-generating system with which the heat diffuser is intended for use. In some embodiments, the resistance to draw (RTD) of the porous body may be between about 10 to 130 mm $H_2O$, or preferably between about 40 to 100 mm $H_2O$. The RTD of a specimen may refer to the static pressure difference between the two ends of the specimen when it may be traversed by an air flow under steady conditions in which the volumetric flow is 17.5 millilitres per second at the output end. The RTD of a specimen may be measured using the method set out in ISO Standard 6565:2002 with any ventilation blocked.

The porous body may be formed from a heat storage material.

The term "heat storage material" refers to a material having a high heat capacity. With this arrangement, the porous body may act as a heat reservoir, allowing the heat diffuser to absorb and store heat from the heating element and to subsequently release the heat over time to the aerosol-forming substrate, via air drawn through the porous body.

Where the porous body is formed from a heat storage material, the porous body may be formed from a material having a specific heat capacity of at least 0.5 J/g·K, or preferably at least 0.7 J/g·K, or more preferably at least 0.8 J/g·K at 25 degrees Celsius and constant pressure. As the specific heat capacity of a material may be effectively a measure of the material's ability to store thermal energy, forming the porous body from a material having a high heat capacity may allow the porous body to provide a large heat reservoir for heating air drawn through the heat diffuser without substantially increasing the weight of an aerosol-generating system with which the heat diffuser may be intended for use.

The porous body may be formed from any suitable material or materials. Where the porous body is formed from a heat storage material, suitable materials may include, but may not limited to, glass fibre, glass mat, ceramic, silica, alumina, carbon, and minerals, or any combination thereof.

The heat storage material may be thermally insulating. As used herein, the term "thermally insulating" refers to a material having a thermal conductivity of less than 100 W/m·K, or preferably less than 40 W/m·K, or less than 10 W/m·K at 23 degrees Celsius and a relative humidity of 50%. This may result in a heat diffuser with a higher thermal inertia, relative to thermally conductive heat diffusers, in order to reduce variations in the temperature of air drawn through the porous body that may be caused by temperature fluctuations in the heating element. This may result in more consistent aerosol characteristics.

The porous body may be thermally conductive. As used herein, the term "thermally conductive" refers to a material having a thermal conductivity of at least 10 W/m·K, or preferably at least 40 W/m·K, or more preferably at least 100 W/m·K at 23 degrees Celsius and a relative humidity of 50%. Where the porous body is thermally conductive, the porous body may be formed from a material having a thermal conductivity of at least 40 W/m·K, or preferably at least 100 W/m·K, or more preferably at least 150 W/m·K, or most preferably at least 200 W/m·K at 23 degrees Celsius and a relative humidity of 50%.

Advantageously, this may reduce the thermal inertia of the heat diffuser and allow the temperature of the heat diffuser to quickly adjust to changes in the temperature of the heating element, for example where the heating element may be heated according to a heating regime which may changes over time, while still allowing the air drawn through the porous body to be evenly heated. Further, by having a high thermal conductivity, the thermal resistance through the porous body may be lower. This may allow the temperature of portions of the porous body which may be remote from the heating element in use to be at a similarly high temperature as the portions of the porous body which are closest to the heating element in use. This may provide for particularly efficient heating of air drawn through the porous body.

Where the porous body is thermally conductive, the porous body may be formed from a material having a thermal conductivity of at least 40 W/m·K, or preferably at least 100 W/m·K, or more preferably at least 150 W/m·K, or most preferably at least 200 W/m·K at 23 degrees Celsius and a relative humidity of 50%.

Where the porous body is thermally conductive, suitable thermally conductive materials may include, but are not limited to, aluminium, copper, zinc, steel, silver, thermally conductive polymers, or any combination or alloy thereof.

In an embodiment, the porous body is formed from a heat storage material which is also thermally conductive, such as aluminium.

In an embodiment in which the heat diffuser does not form part of the aerosol-generating device, the porous body may be configured to be penetrated by an electric heating element forming part of an aerosol-generating device when the heat diffuser is coupled to the aerosol-generating device. The term "penetrated" is used to mean that the heating element at least partially extends into the porous body. Thus, the heating element may be sheathed within the porous body. With this arrangement, by the act of penetration, the heating element may be brought into close proximity to, or contact with, the porous body. This may increase heat transfer between the heating element and the porous body and, consequently, to air drawn through the porous body relative to examples in which the porous body may not be penetrated by the heating element.

The heating element may conveniently be shaped as a needle, pin, rod, or blade that may be inserted into the heat diffuser. The aerosol-generating device may comprise more than one heating element, and in this document a heating element mean one or more heating elements.

The porous body may define a cavity or hole for receiving the electric heating element when the heat diffuser may be coupled to the aerosol-generating device.

In an embodiment, the porous body may be rigid.

The porous body may be pierceable by the heating element when the heat diffuser is coupled to the aerosol-generating device. For example, the porous body may comprise a foam, such as a polymer, metal or ceramic foam, that is pierceable by the heating element.

In an embodiment, the electric heating element may be provided as part of an aerosol-generating device with which the heat diffuser is intended for use, or as part of the aerosol-generating article with which the heat diffuser is intended for use, as part of the heat diffuser, or any combination thereof. The electric heating element may be coupled to the porous body of the heat diffuser. The heat diffuser may comprise an electric heating element thermally coupled to the porous body. In such embodiments, the porous body is arranged to absorb heat from the heating element and transfer it to air drawn through the porous body. With this arrangement, the heating element may be easily replaced by replacing the heat diffuser, while allowing the aerosol-generating device to be reused with a new heat diffuser.

The electric heating element may include one or more external heating elements, one or more internal heating elements, or one or more external heating elements, and one or more internal heating elements. As used herein, the term "external heating element" refers to a heating element that is positioned outside of the heat diffuser when an aerosol-generating system including the heat diffuser is assembled. As used herein, the term "internal heating element" refers to a heating element that is positioned at least partially within the heat diffuser, when an aerosol-generating system including the heat diffuser is assembled. The electric heating element may be embedded in the porous body of the heat diffuser.

The one or more external heating elements may include an array of external heating elements that may be arranged around the periphery of the heat diffuser, for example on the outer surface of the porous body. In certain examples, the external heating elements may extend along the longitudinal direction of the heat diffuser. With this arrangement, the heating elements may extend along the same direction in which the heat diffuser may be inserted into and removed from a cavity in an aerosol-generating device. This may reduce interference between the heating elements and the aerosol-generating device relative to devices in which the heating elements may not be aligned with the length of the heat diffuser. In an embodiment, the external heating elements may extend along the length direction of the heat diffuser and may be spaced apart in the circumferential direction. Where the heating element includes one or more internal heating elements, the one or more internal heating elements may include any suitable number of heating elements. For example, the heating element may include a single internal heating element. The single internal heating element may extend along the longitudinal direction of the heat diffuser.

Where the electric heating element forms part of the heat diffuser, the heat diffuser may further include one or more electrical contacts by which the electric heating element may be connectable to a power supply, for example a power supply in the aerosol-generating device.

The electric heating element may be an electrically resistive heating element.

The electric heating element may include a susceptor in thermal contact with the porous body. The electric heating element may be a susceptor forming part of the heat diffuser. In an embodiment, the susceptor may be embedded in the porous body.

The term 'susceptor' refers to a material that can convert electromagnetic energy into heat. When located within a fluctuating electromagnetic field, eddy currents induced in the susceptor may cause heating of the susceptor. As the susceptor is in thermal contact with the heat diffuser, the heat diffuser may be heated by the susceptor.

In such embodiments, the heat diffuser may be designed to engage with an electrically-operated aerosol-generating device including an induction heating source. The induction heating source, or inductor, may generate the fluctuating electromagnetic field for heating a susceptor located within the fluctuating electromagnetic field. In use, the heat diffuser may engage with the aerosol-generating device such that the susceptor may be located within the fluctuating electromagnetic field generated by the inductor.

The susceptor may be in the form of a pin, rod, or blade. The susceptor may have a length of between 5 mm and 15 mm, or for example between 6 mm and 12 mm, or between 8 mm and 10 mm. The susceptor may have a width of between 1 mm and 5 mm and may have a thickness of between 0.01 mm and 2 mm, or for example between 0.5 mm and 2 mm. In an embodiment, the susceptor may have a thickness of between 10 micrometres and 500 micrometres, or more preferably between 10 and 100 micrometres. If the susceptor has a constant cross-section, for example a circular cross-section, it may have a width or diameter of between 1 mm and 5 mm.

The susceptor may be formed from any material that can be inductively heated to a temperature sufficient to generate an aerosol from the aerosol-forming substrate downstream of the heat diffuser. Susceptors may include a metal or carbon. In an embodiment, a susceptor may include a ferromagnetic material, for example ferritic iron, or a ferromagnetic steel, or stainless steel. A suitable susceptor may be, or include, aluminium. Susceptors may be formed from 400 series stainless steels, for example grade 410, or grade 420, or grade 430 stainless steel. Different materials may dissipate different amounts of energy when positioned within electromagnetic fields having similar values of frequency and field strength. Thus, parameters of the susceptor such as material type, length, width, and thickness may all be altered to provide a desired power dissipation within a known electromagnetic field.

Susceptors may be heated to a temperature in excess of 250 degrees Centigrade. Suitable susceptors may include a non-metallic core with a metal layer disposed on the non-metallic core, for example metallic tracks formed on a surface of a ceramic core.

A susceptor may have a protective external layer, for example a protective ceramic layer or protective glass layer encapsulating the susceptor. The susceptor may include a protective coating formed by a glass, a ceramic, or an inert metal, formed over a core of the susceptor.

The heat diffuser may contain a single susceptor. Alternatively, the heat diffuser may include more than one susceptor.

Heat diffusers may include a piercing member at one end of the porous body. This may allow the heat diffuser to conveniently and easily pierce a seal at an end of an aerosol-generating article with which it is intended for use when the heat diffuser is engaged with the aerosol-generating article. Where the aerosol-generating article with which the heat diffuser may include a frangible capsule, for example a frangible capsule containing an aerosol-forming substrate, the piercing member may allow the heat diffuser to conveniently and easily pierce the frangible capsule when the heat diffuser is engaged with the aerosol-generating article.

The downstream end of the piercing member may have a cross-sectional area that may be smaller than the cross-sectional area of the region of the piercing member immediately upstream of the downstream end. In an embodiment, the cross-sectional area of the piercing member may narrow towards a tapered tip at its downstream end.

The piercing member may be formed by the porous body. Alternatively, the piercing member may be a separate element attached at the downstream end of the porous body.

The aerosol-forming substrate may be a solid aerosol-forming substrate. Alternatively, the aerosol-forming substrate may include both solid and liquid elements. The aerosol-forming substrate may include tobacco. The aerosol-forming substrate may include a tobacco-containing material containing volatile tobacco flavor compounds which may be released from the substrate upon heating. The aerosol-forming substrate may include a non-tobacco material. The aerosol-forming substrate may include a tobacco-containing material and a non-tobacco containing material.

The aerosol-forming substrate may further include an aerosol former that may facilitate the formation of a dense and stable aerosol. Examples of suitable aerosol formers may include glycerine and propylene glycol.

The aerosol-forming substrate may include a solid aerosol-forming substrate. The aerosol-forming substrate may include a tobacco-containing material containing volatile tobacco flavor compounds which may be released from the substrate upon heating. The aerosol-forming substrate may include a non-tobacco material.

The aerosol-forming substrate may include at least one aerosol former. As used herein, the term 'aerosol former' is used to describe any suitable known compound or mixture of compounds that, in use, facilitates formation of an aerosol. Suitable aerosol formers are substantially resistant to thermal degradation at the operating temperature of the aerosol-generating article. Examples of suitable aerosol formers are glycerine and propylene glycol. Suitable aerosol formers may include, but may not be limited to: polyhydric alcohols, such as propylene glycol, triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. In an embodiment, aerosol formers are polyhydric alcohols or mixtures thereof, such as propylene glycol, triethylene glycol, 1,3-butanediol and glycerine. The aerosol-forming substrate may include a single aerosol former. Alternatively, the aerosol-forming substrate may include a combination of two or more aerosol formers. The aerosol-forming substrate may have an aerosol former content of greater than 5 percent on a dry weight basis. The aerosol-forming substrate may have an aerosol former content of between approximately 5 percent and approximately 30 percent on a dry weight basis. The aerosol-forming substrate may have an aerosol former content of approximately 20 percent on a dry weight basis.

The aerosol-forming substrate may include a liquid aerosol-forming substrate. The liquid aerosol-forming substrate may include a nicotine solution. The liquid aerosol-forming substrate may include a tobacco-containing material including volatile tobacco flavor compounds, which are released from the liquid upon heating. The liquid aerosol-forming substrate may include a non-tobacco material. The liquid aerosol-forming substrate may include water, solvents, ethanol, plant extracts and natural or artificial flavors. The liquid aerosol-forming substrate may further include an aerosol former.

In an embodiment, the aerosol-generating article may include a liquid aerosol-forming substrate and a liquid retention medium for retaining the liquid aerosol-forming substrate.

The liquid retention medium may include an absorbent material, for example an absorbent polymeric material. Examples of suitable liquid retention materials may include fibrous polymers and porous polymers, such as open-cell foams. The liquid retention medium may include a fibrous cellulose acetate or a fibrous cellulose polymer. The liquid retention medium may include a porous polypropylene material. Other well-known suitable materials capable of retaining a liquid may be used.

The liquid retention medium may either be located within an air-flow path through the heated aerosol-generating article, or may define at least a portion of an air-flow path through the aerosol-generating article. In an embodiment, one or more holes defined through the liquid retention medium may define a portion of the air-flow path through the heated aerosol-generating article between the distal end of the article and the outlet end of the article.

The liquid retention medium may be in the form of a tube having a central lumen. Walls of the tube may be formed from, or include, a suitable liquid-retention material.

The liquid aerosol-forming substrate may be incorporated into the liquid retention medium immediately prior to use. For example, a dose of liquid aerosol-forming substrate may be injected into the liquid retention medium immediately prior to use.

Articles according to the invention may include a liquid aerosol-forming substrate contained within a frangible capsule. The frangible capsule is described in greater detail below. In an embodiment, the aerosol-forming substrate is a liquid aerosol-forming substrate, and the article may further include a frangible capsule containing the liquid aerosol-forming substrate, and a liquid retention medium downstream of the heat diffuser may be arranged to absorb the liquid aerosol-forming substrate when the frangible capsule may be broken.

The frangible capsule may be located within the porous carrier material. For example, the porous carrier material may be provided in the form of a liquid retention tube and the frangible capsule may be located within the lumen of the tube.

The frangible capsule may be located adjacent to the liquid retention medium within the article such that the liquid-aerosol-forming substrate may be released from the frangible capsule and may contact and be retained by the liquid retention medium. The frangible capsule may be located within the liquid retention medium. For example, the liquid retention medium may include a plug of material in which the capsule may be embedded. In an embodiment, an article including a tubular liquid retention medium, and the frangible capsule containing the liquid aerosol-forming substrate, may be located within the lumen of the tubular liquid retention medium.

Where the aerosol-forming substrate is a solid aerosol-forming substrate, the solid aerosol-forming substrate may be immediately downstream of the heat diffuser. For example, the solid aerosol-forming substrate may abut the heat diffuser. In an embodiment, the solid aerosol-forming substrate may be spaced apart in the longitudinal direction from the heat diffuser.

In an embodiment, the aerosol-forming substrate may be a liquid aerosol-forming substrate, and the article may further include a liquid retention medium for retaining the liquid aerosol-forming substrate. In an embodiment, the liquid retention medium may be immediately downstream of the heat diffuser. For example, the liquid retention medium may abut the heat diffuser. In an embodiment, the liquid retention medium may be spaced apart in the longitudinal direction from the heat diffuser.

In an embodiment, the aerosol-forming substrate may be a liquid aerosol-forming substrate, and the article further may include a liquid retention medium for retaining the liquid aerosol-forming substrate, where the liquid retention medium may be spaced apart in the longitudinal direction from the heat diffuser.

With this arrangement, conductive heat transfer between the heat diffuser and the liquid retention medium, or a solid aerosol-forming substrate, may be reduced. This may further reduce or prevent areas of local high temperature, or "hot spots", from occurring in the liquid retention medium, or the aerosol-forming substrate, that may otherwise be caused by conductive heating.

Aerosol-generating articles may further include a support element that may be located immediately downstream of the aerosol-forming substrate or, where the article include a liquid retention medium for retaining a liquid aerosol-forming substrate, immediately downstream of the liquid retention medium. The support element may abut the aerosol-forming substrate or the liquid retention medium.

The support element may be formed from any suitable material, or combination of materials. For example, the support element may be formed from one or more materials selected from the group consisting of: cellulose acetate; cardboard; crimped paper, such as crimped heat resistant paper or crimped parchment paper; and polymeric materials, such as low density polyethylene (LDPE). In an embodiment, the support element may be formed from cellulose acetate. The support element may include a hollow tubular element. For example, the support element may include a hollow cellulose acetate tube. The support element may have an external diameter that may be approximately equal to the external diameter of the aerosol-generating article.

The support element may have an external diameter of between approximately 5 millimetres and approximately 12 millimetres, or for example of between approximately 5 millimetres and approximately 10 millimetres, or between approximately 6 millimetres and approximately 8 millimetres. For example, the support element may have an external diameter of 7.2 millimetres+/−10 percent.

The support element may have a length of between approximately 5 millimetres and approximately 15 mm. In an embodiment, the support element may have a length of approximately 8 millimetres.

An aerosol-cooling element may be located downstream of the aerosol-forming substrate. For example, an aerosol-cooling element may be located immediately downstream of a support element, and may abut the support element. The aerosol-cooling element may be located immediately downstream of the aerosol-forming substrate or, where the article includes a liquid retention medium for retaining a liquid aerosol-forming substrate, immediately downstream of the liquid retention medium. For example, the aerosol-cooling element may abut the aerosol-forming substrate or the liquid retention medium.

The aerosol-cooling element may have a total surface area of between approximately 300 square millimetres per millimetre length and approximately 1000 square millimetres per millimetre length. In an embodiment, the aerosol-cooling element may have a total surface area of approximately 500 square millimetres per millimetre length.

The aerosol-cooling element may have a low resistance to draw. That is, the aerosol-cooling element may offer a low resistance to the passage of air through the aerosol-generating article. In an embodiment, the aerosol-cooling element may not substantially affect the resistance to draw of the aerosol-generating article.

The aerosol-cooling element may include a plurality of longitudinally extending channels. The plurality of longitudinally extending channels may be defined by a sheet material that may have been one or more of crimped, pleated, gathered and folded to form the channels. The plurality of longitudinally extending channels may be defined by a single sheet that may have been one or more of crimped, pleated, gathered and folded to form multiple channels. Alternatively, the plurality of longitudinally extending channels may be defined by multiple sheets that may have been one or more of crimped, pleated, gathered and folded to form multiple channels.

In an embodiment, the aerosol-cooling element may include a gathered sheet of material selected from the group consisting of metallic foil, polymeric material, and substantially non-porous paper or cardboard. In an embodiment, the aerosol-cooling element may include a gathered sheet of material selected from the group consisting of polyethylene (PE), polypropylene (PP), polyvinylchloride (PVC), polyethylene terephthalate (PET), polylactic acid (PLA), cellulose acetate (CA), and aluminium foil.

In an embodiment, the aerosol-cooling element includes a gathered sheet of biodegradable material. For example, a gathered sheet of non-porous paper or a gathered sheet of biodegradable polymeric material, such as polylactic acid or any well-known commercially available family of starch based copolyesters. In an embodiment, the aerosol-cooling element includes a gathered sheet of polylactic acid.

The aerosol-cooling element may be formed from a gathered sheet of material having a specific surface area of between approximately 10 square millimetres per milligram and approximately 100 square millimetres per milligram weight. In an embodiment, the aerosol-cooling element may be formed from a gathered sheet of material having a specific surface area of approximately 35 mm$^2$/mg.

In use, the aerosol-cooling element may be arranged and configured to cool the heated air and vapor drawn through the element to between about 80 degrees Celsius and 120 degrees Celsius. In an embodiment, the aerosol-cooling element cools the heated air and vapor drawn through the element to about 100 degrees Celsius.

The aerosol-generating article may include a mouthpiece located at the outlet end of the aerosol-generating article. The mouthpiece may be located immediately downstream of an aerosol-cooling element, and may abut the aerosol-cooling element. The mouthpiece may be located immediately downstream of the aerosol-forming substrate or, where the article includes a liquid retention medium for retaining a liquid aerosol-forming substrate, immediately downstream of the liquid retention medium. In an embodiment, the mouthpiece may abut the aerosol-forming substrate, or the liquid retention medium. The mouthpiece may include a filter. The filter may be formed from one or more suitable filtration materials. The filtration materials may be any well-known material used for filtration purposes. In an embodiment, the mouthpiece may include a filter formed from cellulose acetate tow.

The mouthpiece may have an external diameter that may be approximately equal to the external diameter of the aerosol-generating article. The mouthpiece may have an external diameter between approximately 5 millimetres and approximately 10 millimetres, or between approximately 6 millimetres and approximately 8 millimetres. In an embodiment, the mouthpiece may have an external diameter of 7.2 millimetres+/−10%.

The mouthpiece may have a length of between approximately 5 millimetres and approximately 20 millimetres. For example, the mouthpiece may have a length of from about 7 mm to about 12 mm.

The elements of the aerosol-forming article may be circumscribed by an outer wrapper, for example in the form of a rod. The wrapper may circumscribe at least a downstream portion of the heat diffuser. In an embodiment, the wrapper may circumscribe the heat diffuser along substantially the entire length of the heat diffuser. The outer wrapper may be formed from any suitable material or combination of materials. The outer wrapper may be non-porous. The outer wrapper may be liquid-impervious.

The aerosol-generating article may be substantially cylindrical in shape. The aerosol-generating article may be substantially elongate. The aerosol-generating article may have a length and a circumference substantially perpendicular to the length. The aerosol-forming substrate or a porous carrier material in which the aerosol-forming substrate may be absorbed during use, may be substantially cylindrical in shape. The aerosol-forming substrate or the porous carrier material may be substantially elongate. The aerosol-forming substrate, or the porous carrier material, may also have a length and a circumference substantially perpendicular to the length.

The aerosol-forming substrate or, where applicable, the liquid retention medium, may have a length of between about 7 mm and about 15 mm. In an embodiment, the aerosol-forming substrate, or the liquid retention medium, may have a length of approximately 10 mm. Alternatively, the aerosol-forming substrate, or the liquid retention medium, may have a length of approximately 12 mm.

The aerosol-generating substrate or liquid retention medium, may have an external diameter that may be approximately equal to the external diameter of the aerosol-generating article. The external diameter of the aerosol-forming substrate, or the liquid retention medium, may be between approximately 5 mm and approximately 12 mm. In an embodiment, the aerosol-forming substrate, or the liquid retention medium, may have an external diameter of approximately 7.2 mm+/−10 percent.

A heated aerosol-generating system may include an aerosol-generating device and a heated aerosol-generating article that may include any combination of the aerosol-generating devices and a heated aerosol-generating articles described herein. The aerosol-generating device may be an electrically operated aerosol-generating device.

An aerosol-generating device may be a heated aerosol-generating device, which may be an aerosol-generating device including a heating element or heater. The heating element or heater may be used to heat an aerosol-forming substrate of an aerosol-generating article to generate an aerosol.

The aerosol-generating device may be an electrically heated aerosol-generating device, which may be an aerosol-generating device including a heating element that may be operated by electrical power to heat an aerosol-forming substrate of an aerosol-generating article to generate an aerosol.

The aerosol-generating device may include electric circuitry configured to control the supply of power from a power supply to an electric heating element of the system.

The aerosol-generating device of the aerosol-generating system may include: a housing having a cavity for receiving the heated aerosol-generating article and a controller configured to control the supply of power from a power supply to an electric heating element of the system.

The electric heating element may include one or more heating elements.

In an embodiment, the electrically operated aerosol-generating device may include an electric heating element and a housing having a cavity, and wherein the heated aerosol-generating article may be received in the cavity. The heating element may conveniently be shaped as a needle, pin, rod, or blade that may be inserted into the article.

Aerosol-generating systems may include an electric heating element. The electric heating element may include one or more external heating elements, one or more internal heating elements, or one or more external heating elements and one or more internal heating elements. As used herein, the term "external heating element" may refer to a heating element that may be positioned outside of the heat diffuser when an aerosol-generating system including the heat diffuser may be assembled. As used herein, the term "internal heating element" refer to a heating element that may be positioned at least partially within the heat diffuser when an aerosol-generating system including the heat diffuser may be assembled.

The one or more external heating elements may include an array of external heating elements arranged around the inner surface of the cavity. In an embodiment, the external heating elements may extend along the longitudinal direction of the cavity. With this arrangement, the heating elements may extend along the same direction in which the heat diffuser and the article may be inserted into and removed from the cavity. This may reduce interference between the heating elements and the heat diffuser relative to devices in which the heating elements may not be aligned with the length of the cavity. In an embodiment, the external heating elements may extend along the length direction of the cavity and may be spaced apart in the circumferential direction. Where the heating element includes one or more internal heating elements, the one or more internal heating elements may include any suitable number of heating elements. For example, the heating element may include a single internal heating element. The single internal heating element may extend along the longitudinal direction of the cavity.

The electric heating element may include an electrically resistive material. Suitable electrically resistive materials may include, but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may include doped or undoped ceramics. Examples of suitable doped ceramics include doped silicon carbides. Examples of suitable metals include titanium, zirconium, tantalum and metals from the platinum group. Examples of suitable metal alloys may include stainless steel, copper, nickel, cobalt, chromium, aluminium, titanium, zirconium, hafnium, niobium, molybdenum, tantalum, tungsten, tin, gallium, manganese, and iron-containing alloys, and super-alloys based on nickel, iron, cobalt, stainless steel, iron-aluminium based alloys and iron-manganese-aluminium based alloys. In composite materials, the electrically resistive material may optionally be embedded in, encapsulated or coated with an insulating material or vice-versa, depending on the kinetics of energy transfer and the external physicochemical properties required. The heating element may include a metallic etched foil insulated between two layers of an inert material. In that case, the inert material may include commercially available polyimide films, all-polyimide or mica foil.

Where the electric heating element includes a susceptor in thermal contact with the porous body of the heat diffuser, the aerosol-generating device may include an inductor arranged to generate a fluctuating electromagnetic field within the cavity and an electrical power supply connected to the inductor. The inductor may include one or more coils that may generate a fluctuating electromagnetic field. The coil or coils may surround the cavity.

The device may be capable of generating a fluctuating electromagnetic field of between 1 and 30 MHz, for example, between 2 and 10 MHz, for example between 5 and 7 MHz. In an embodiment, the device may be capable of generating a fluctuating electromagnetic field having a field strength (H-field) of between 1 and 5 kA/m, for example between 2 and 3 kA/m, for example about 2.5 kA/m.

In an embodiment, the aerosol-generating device may be a portable or handheld aerosol-generating device.

The aerosol-generating device may be substantially cylindrical in shape

The aerosol-generating device may have a length of between approximately 70 millimetres and approximately 120 millimetres.

The device may include a power supply for supplying electrical power to the electric heating element. The power supply may be any suitable power supply, for example a DC voltage source such as a battery. In one embodiment, the power supply may be a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

The device may include electric circuitry for controlling the supply of power from the power supply to the electric heating element. The electric circuitry may include one or more microprocessors or microcontrollers.

As used herein, the terms 'upstream' and 'downstream' may be used to describe the relative positions of elements, or portions of elements, of the heat diffuser, aerosol-generating article, or aerosol-generating device, in relation to the direction in which air may be drawn through the system during use thereof.

As used herein, the term 'longitudinal' may be used to describe the direction between the upstream end and the downstream end of the heat diffuser, aerosol-generating article, or aerosol-generating device and the term 'transverse' may be used to describe the direction perpendicular to the longitudinal direction.

As used herein, the term 'diameter' may be used to describe the maximum dimension in the transverse direction of the heat diffuser, aerosol-generating article, or aerosol-generating device. As used herein, the term 'length' may be used to describe the maximum dimension in the longitudinal direction.

An aerosol-generating article may be used together with an aerosol-generating device described above, or with an aerosol generating device according to another embodiment. The aerosol-generating article may also be used with other aerosol generating devices (not described in this document).

The heated aerosol-generating article may be referred to herein as an article. In one embodiment, the article may include a plurality of elements which may be coaxially aligned and assembled within a wrapper. The article may have an outlet end and a distal end upstream from the outlet end. The article may include a liquid aerosol-forming substrate and a liquid retention medium for retaining the liquid aerosol-forming substrate. The wrapper may be formed from a sheet of liquid-impervious material.

In an embodiment, a heated aerosol-generating article may use a solid aerosol-forming substrate that may be formed in the shape of a rod. The wrapper that may be used to assemble or circumscribe the elements of such articles may be a traditional porous cigarette paper. The use of a liquid aerosol-forming substrate may provide certain benefits over the use of a solid aerosol-forming substrate. One such benefit is the greater variety of flavors that may be provided in liquid substrate formulations, as compared to solid substrate formulations. Another benefit may be the lower environmental odour associated with the vaporization of liquid substrates. However, it is desirable to provide a liquid aerosol-forming substrate in a consumable design that may have a cigarette look and feel. The use of an article that has a plurality of elements may include a liquid retention medium for retaining a liquid aerosol-forming substrate, and which may be assembled within a liquid-impervious wrapper to provide an advantage of an e-cigarette type system with the look, feel, and convenience of a heated tobacco system.

In an embodiment, the wrapper may be a sheet of polymeric material, a sheet of treated paper, for example a polymer coated paper or a polymer impregnated paper, or a sheet of metallic foil. The wrapper may be a sheet of hydrophobic material such as a wax coated paper. In an embodiment, a liquid impervious wrapper may be formed from, or include, an aluminium laminate paper, a class of paper that is well-known in the confectionary industry and used for an inner liner in tobacco boxes. The liquid impervious wrapper may be referred to as a liquid impermeable wrapper.

In one embodiment, the article is configured to be suitable for use with an electrically-operated aerosol-generating device. The article may be a consumable article having an outlet end, a distal end upstream from the outlet end, and a mid-point located an approximately equal distance between the outlet end and the distal end. The article may include a liquid retention medium, at least a portion of which may be located between the distal end and the mid-point.

In one embodiment, the article may include a liquid aerosol-forming substrate contained within a frangible capsule, where the frangible capsule may be located between the distal end and the mid-point. The article may be configured such that, during use, air can be drawn through the article from the distal end to the outlet end.

In an embodiment, the liquid aerosol-forming substrate may be releasably contained within the frangible capsule and the liquid retention medium may be located in proximity to the frangible capsule for retaining the liquid aerosol-forming substrate within the article after its release from the frangible capsule.

The liquid aerosol-forming substrate may, alternatively, be incorporated into the liquid retention medium immediately prior to use. For example, a dose of liquid aerosol-forming substrate may be injected into the liquid retention medium immediately prior to use.

In one embodiment, the article may include a first volatile liquid substrate contained within a first frangible capsule, and a second volatile liquid substrate contained within a second frangible capsule. The first and second frangible capsules may be located between the distal end and the mid-point. The article may be configured such that, during use, air may be drawn through the article from the distal end to the outlet end.

In an embodiment, the first volatile liquid substrate may be releasably contained within the first frangible capsule and the liquid retention medium may be located in proximity to the first frangible capsule for retaining the first volatile liquid substrate within the article after it may be released from the first frangible capsule. In an embodiment, the second volatile liquid substrate may be releasably contained within the second frangible capsule and the liquid retention medium may be located in proximity to the second frangible capsule for retaining the second volatile liquid substrate within the article after its release from the second frangible capsule.

The article may include a liquid aerosol-forming substrate. The first volatile liquid substrate may be a liquid aerosol-forming substrate, or may be a constituent part of a liquid aerosol-forming substrate, such as a liquid aerosol former or a nicotine source. The second volatile liquid substrate may also be a liquid aerosol-forming substrate, or may be a constituent part of a liquid aerosol-forming substrate, such as an aerosol former or a nicotine source.

The liquid first volatile substrate may be a first liquid aerosol-forming substrate and the second liquid volatile substrate may be a second liquid aerosol-forming substrate, where the first liquid aerosol-forming substrate may have a different composition to the second liquid aerosol-forming substrate. This may provide two different sensorial experiences using the same article. However, the first liquid aerosol-forming substrate may have the same composition as the second liquid aerosol-forming substrate.

The first volatile liquid substrate may be a constituent part of a liquid aerosol-forming substrate and the second volatile liquid substrate may be another constituent part of the aerosol-forming substrate, where the first volatile substrate and the second volatile substrate may combine to form the liquid aerosol-forming substrate.

The heated aerosol-generating article may be a consumable that may be consumed by coupling or engaging with an aerosol-generating device, and may be an electrically-operated aerosol-generating device. The article may be removably couplable with the aerosol-generating device. The article may be used once or twice and then disposed of. A number of uses may depend on a number of frangible capsules provided. A method of using the heated aerosol-generating article may include the steps of coupling the article to an aerosol-generating device, activating a heating structure of the aerosol-generating device, and drawing air through the heated aerosol-generating article. Liquid aerosol-forming substrate retained within the aerosol-generating article may then be vaporized by heat energy supplied by the heating structure and condensed to form an aerosol entrained in the air. When the aerosol-forming substrate may have been consumed, the article may be removed from the device. In an embodiment, the method may include steps of releasing the liquid aerosol-forming substrate from a frangible capsule, such that it may be retained by the liquid retention medium of the article, coupling the article to an electrically-operated aerosol-generating device, activating a heating structure of the electrically-operated aerosol-generating device, and drawing air through the article, where the liquid aerosol-forming substrate may be vaporized by heat energy supplied by the heating structure and condensed to form an aerosol entrained in the air. In one embodiment, a method may include steps of releasing at least one of the first volatile liquid substrate from a first frangible capsule and the second liquid volatile substrate from a second frangible capsule such that it may be retained by the liquid retention medium of the article, coupling the article to an electrically-operated aerosol-generating device, activating a heating structure of the electrically-operated aerosol-generating device, and drawing air through the article, the liquid retained by the liquid retention medium being vaporized by heat energy supplied by the heating structure and condensing to form an aerosol entrained in the air.

In an embodiment, the heating structure may heat air that may be drawn into the heated aerosol-generating device, the heated air passing over or through the liquid retention medium of the article to vaporize the liquid aerosol-forming substrate and allow formation of an aerosol. The air may be heated to a temperature of about 200° C. to 220° C. before passing over or through the liquid retention medium. In an embodiment, the air with entrained volatile elements may subsequently cool to a temperature of about 100° C. within the article, allowing the volatile elements to condense and form an aerosol. The heating structure may alternatively heat the liquid retention medium by conduction or radiation in order to vaporize the liquid aerosol-forming substrate and allow formation of an aerosol.

Where the first liquid volatile substrate includes a first liquid aerosol-forming substrate and the second liquid volatile substrate includes a second liquid aerosol-forming substrate, a method of using the heated aerosol generating article may include: releasing the first liquid aerosol-forming substrate from the first frangible capsule such that it may be retained by the liquid retention medium; coupling the heated aerosol-generating article to an electrically-operated aerosol-generating device; activating a heating structure of the electrically-operated aerosol-generating device; drawing air through the heated aerosol-generating device, the first liquid aerosol-forming substrate being vaporized by heat energy supplied by the heating structure and condensing to form an aerosol entrained in the air; uncoupling the heated aerosol-generating article from the electrically operated aerosol-generating device; releasing the second liquid aerosol-forming substrate from the second frangible capsule such that it may be retained by the liquid retention medium; coupling the heated aerosol-generating article to the electrically-operated aerosol-generating device; activating the heating structure of the electrically-operated aerosol-generating device; and drawing air through the heated aerosol-generating device, the second liquid aerosol-forming substrate being vaporized by heat energy supplied by the heating structure and condensed to form an aerosol entrained in the air.

Where the first liquid volatile substrate includes a first constituent of a liquid aerosol-forming substrate and the second liquid volatile substrate includes a second constituent of the liquid aerosol-forming substrate, a method of using the heated aerosol-generating article may include: releasing the first liquid volatile substrate from the first frangible capsule such that it may be retained by the liquid retention medium; releasing the second liquid volatile substrate from the second frangible capsule such that it may be retained by the liquid retention medium, and combining with the first liquid volatile substrate to form a liquid aerosol-forming substrate; coupling the heated aerosol-generating article to an electrically-operated aerosol-generating device; activating a heating structure of the electrically-operated aerosol-generating device; and drawing air through the heated aerosol-generating device, the liquid aerosol-forming substrate being vaporized by heat energy supplied by the heating structure and condensed to form an aerosol entrained in the air.

In an embodiment, the heating structure may heat air that may be drawn into the heated aerosol-generating device, the heated air passing over or through the liquid retention medium to allow formation of an aerosol. However, the heating structure may heat the liquid retention medium by conduction or radiation to allow formation of an aerosol.

As the article may be intended to be disposed after one or two uses, the hygiene issues that may be associated with typical e-cigarette systems may be overcome. Furthermore, the liquid aerosol-forming substrate may not directly contact a heating element and, thus, problems with overheating of the aerosol-forming substrate may not occur. The liquid impervious wrapper, if provided, may help to prevent leakage of liquid aerosol-forming substrate. Articles may be produced with a wide range of different liquid aerosol-forming substrate compositions, thereby providing a wide range of flavors and experiences that may be provided by e-cigarette systems. In particular, where a first volatile liquid substrate may include a first liquid aerosol-forming substrate and a second volatile liquid substrate may include a second liquid aerosol-forming substrate, the article may be provided with multiple liquid aerosol-forming substrate compositions, and thereby provide multiple flavors and experiences. In an embodiment, the articles may be consumed using aerosol-generating devices configured for heating aerosol-generating articles including solid aerosol-forming substrates. Thus, an adult vaper may select either a tobacco containing heated aerosol-generating article or select an article containing a liquid aerosol-forming substrate.

As used herein, the term "volatile substrate" refers to an aerosol-forming substrate or a constituent part of an aerosol-forming substrate.

As used herein, the term "aerosol-forming substrate" refers to a substrate capable of releasing volatile compounds that may form an aerosol. An aerosol-forming substrate may be solid or liquid or comprise both solid and liquid elements.

As used herein, the term "liquid aerosol-forming substrate" refers to an aerosol-forming substrate that may be in a liquid rather than a solid form. A liquid aerosol-forming substrate may be at least partially absorbed by a liquid retention medium. A liquid-aerosol-forming substrate may include an aerosol-forming substrate in the form of a gel. Similarly, the term "liquid volatile substrate" may refer to a substrate that is in a liquid rather than a solid form.

As used herein, the term "outlet end" refers to a portion of the heated aerosol-generating article where aerosol exits the article.

As used herein, the term "distal end" refers to an end of the article that opposes the outlet end.

As used herein, the terms "upstream" and "downstream" are used to describe the relative positions of elements, or portions of elements, of the heated aerosol-generating article in relation to the direction that air may be drawn through the article or system during use. The outlet end of the article may also be referred to as the downstream end, and the distal end of the article may also be referred to as the upstream end. Elements, or portions of elements, of the article may be described as being upstream or downstream of one another based on their relative positions between the mouth or downstream end and the distal or upstream end.

As used herein, the term "liquid-impervious" refers to the wrapper, and may indicate that aqueous liquids may not pass through the wrapper under typical operating conditions.

As used herein, the term 'sheet' denotes a laminar element that may have a width and length substantially greater than the thickness thereof. The width of a sheet may be greater than 10 mm, or may be greater than 20 mm or 30 mm.

As used herein, the term 'longitudinal' is used to describe the direction between the upstream end and the downstream end of the aerosol-generating article or aerosol-generating device, and the term 'transverse' may be used to describe the direction perpendicular to the longitudinal direction.

As used herein, the term 'diameter' is used to describe the maximum dimension in the transverse direction of the aerosol-generating article or aerosol-generating device. As used herein, the term 'length' may be used to describe the maximum dimension in the longitudinal direction.

As used herein, the term "liquid retention medium" refers to an element that may be capable of releasably retaining a liquid aerosol-forming substrate. The liquid retention medium may be, or may comprise, a porous or fibrous material that may absorb or otherwise retain a liquid aerosol-forming substrate that may be brought into contact with while allowing the liquid aerosol-forming substrate to be released by vaporization.

As used herein, the term "frangible capsule" refers to a capsule that may be capable of containing a liquid aerosol-forming substrate and releasing the liquid aerosol-forming substrate when broken or ruptured. The frangible capsule may be formed from, or comprise, a brittle material that may be easily broken to release its liquid aerosol-forming substrate contents. For example the capsule may be broken by external force such as finger pressure, or by contact with a piercing or rupturing element.

The heated aerosol-generating article may be substantially cylindrical in shape. The aerosol-generating article may be substantially elongate. The aerosol-generating article may have a length and a circumference substantially perpendicular to the length. The liquid retention medium may be substantially cylindrical in shape. The liquid retention medium may be substantially elongate. The liquid retention medium may also have a length and a circumference substantially perpendicular to the length.

The aerosol-generating article may have an external diameter of between approximately 5 millimetres and approximately 12 millimetres, for example of between approximately 6 millimetres and approximately 8 millimetres. In an embodiment, the aerosol-generating article may have an external diameter of 7.2 millimetres+/−10 percent.

The aerosol-generating article may have a total length between approximately 25 mm and approximately 100 mm. The aerosol-generating article may have a total length between approximately 30 mm and approximately 100 mm. In one embodiment, the aerosol-generating article may have a total length of approximately 45 mm. In another embodiment, the aerosol-generating article may have a total length of approximately 33 mm.

The liquid retention medium may have a length of between about 7 mm and about 20 mm, for example between 8 mm and 15 mm. In one embodiment, the liquid retention medium may have a length of approximately 10 mm.

The heated aerosol-generating article may include a plurality of elements assembled by, or circumscribed by, a wrapper in the form of a rod. For example, the article may include the liquid retention medium, and a mouthpiece located downstream of the liquid retention medium. The wrapper may include indicators, such as markings at positions along its length to indicate the location of the frangible capsule or of the first and second frangible capsules. The indicators may indicate where to apply pressure to rupture or break the frangible capsule, or the first frangible capsule and the second frangible capsule respectively.

The mouthpiece may be located at the outlet end of the article. The mouthpiece may include a filter. The filter may be formed from one or more suitable filtration materials. Many such filtration materials may be well-known in the art. In one embodiment, the mouthpiece may include a filter formed from cellulose acetate tow.

The article may include a porous or air-permeable plug located at the distal end of the article. Such a plug may act to help retain the liquid aerosol-forming substrate within the article. The plug may have an external diameter of a diameter of between approximately 5 millimetres and approximately 10 millimetres, for example of between approximately 6 millimetres and approximately 8 millimetres. In an embodiment, the plug has an external diameter of 7.2 millimetres+/−10%.

The plug may have a length of between approximately 2 millimetres and approximately 10 millimetres. For example, the mouthpiece may have a length of from about 3 mm to about 5 mm.

The article may include an aerosol-forming section or an aerosol-cooling section. The plurality of elements may be co-axially aligned and assembled within the wrapper. The wrapper may be a traditional cigarette paper. The wrapper may be a polymeric film or a coated paper. The wrapper may be liquid-impervious.

The liquid retention medium may include an absorbent material, for example an absorbent polymeric material. Examples of suitable liquid retention materials include fibrous polymers and porous polymers such as open-cell foams. The liquid retention medium may include a fibrous cellulose acetate or a fibrous cellulose polymer. The liquid retention medium may include a porous polypropylene material. Suitable materials capable of retaining a liquid may be well-known to a skilled person in the art.

The liquid retention medium may be either located within an air-flow path through the heated aerosol-generating article or may define at least a portion of an air-flow path through the aerosol-generating article. In an embodiment, one or more holes defined through the liquid retention medium may define a portion of the air-flow path through the heated aerosol-generating article between the distal end of the article and the outlet end of the article.

The liquid retention medium may be in the form of a tube having a central lumen. Walls of the tube may then be formed from, or comprise, a suitable liquid-retention material.

The heated aerosol-generating article may include a liquid aerosol-forming substrate contained within a frangible capsule. The heated aerosol-generating article may include liquid volatile substrates contained within frangible capsules. The frangible capsule or capsules may be spheroid, for example spherical or ovoid, having a maximum dimension of between 2 mm and 8 mm, for example between 4 mm and 6 mm. The frangible capsule or capsules may contain a volume of between 20 and 300 microliters, for example between 30 and 200 microliters. Such a range may provide between 10 and 150 puffs of aerosol.

In an embodiment, the liquid retention medium may be capable of absorbing between 105% and 110% of the total volume of liquid contained within the frangible capsule. This may help to prevent leakage of liquid aerosol-forming substrate from the article after the frangible capsule has been broken to release its contents. The liquid retention medium may be between 90% and 95% saturated after release of the liquid aerosol-forming substrate from the frangible capsule.

The frangible capsules may have a brittle shell, or may be shaped to facilitate rupture when subjected to external force. The frangible capsules may be configured to be ruptured by application of external force. For example, the frangible capsules may be configured to rupture at a specific defined external force, thereby releasing the liquid-aerosol-forming substrate. The frangible capsules may be configured with a weakened or brittle portion of its shell to facilitate rupture. The frangible capsules may be arranged for engagement with a piercing element for breaking the capsule and releasing the liquid aerosol-forming substrate. The frangible capsules may have a burst strength of between about 0.5 and 2.5 kilograms force (kgf), for example between 1.0 and 2.0 kgf.

The shell of the frangible capsules may include a suitable polymeric material, for example a gelatin based material. The shell of the capsules may include a cellulose material or a starch material.

In an embodiment, the frangible capsule may be located adjacent to the liquid retention medium within the article such that the liquid-aerosol-forming substrate may be released from the frangible capsule and may contact and be retained by the liquid retention medium. The frangible capsule may be located within the liquid retention medium. For example, the liquid retention medium may be in the form of a tube having a lumen and the frangible capsule containing the liquid aerosol-forming substrate may be located within the lumen of the tube.

In one embodiment, the frangible capsules may be located adjacent to the liquid retention medium within the article such that the liquid volatile substrate may be released from the frangible capsule, and may contact and be retained by the liquid retention medium. The frangible capsules may be located within the liquid retention medium. For example, the liquid retention medium may be in the form of a tube having a lumen and the frangible capsules containing the liquid volatile substrate may be located within the lumen of the tube.

In an embodiment, the heated aerosol-generating article may include one or two frangible capsules including liquid volatile substrates. However, the heated aerosol-generating article may include any number of frangible capsules. The heated aerosol-generating article may include two or more frangible capsules comprising liquid volatile substrates.

The heated aerosol-generating article may include an aerosol generation section located downstream of the liquid retention medium. In use, the liquid aerosol-forming substrate may be vaporized and volatile elements of the substrate may be drawn downstream from the liquid retention medium. The volatile elements may then cool in the aerosol forming section to form the inhalable aerosol. In an embodiment, the air with entrained volatile elements may cool to a temperature of about or below 100° C. within the aerosol generation section. The aerosol forming section may be defined by a space within the article, or by the lumen of a tube within the article. The aerosol forming section may include an aerosol-cooling element, for example an aerosol-cooling element including a gathered sheet of polymeric material. A suitable aerosol-cooling element is described above.

As mentioned above, the article may include a liquid aerosol-forming substrate. In an embodiment with two capsules, the first volatile liquid substrate may be a liquid aerosol-forming substrate or may be a constituent part of a liquid aerosol-forming substrate, such as a liquid aerosol former or a nicotine source. The second volatile liquid substrate may also be a liquid aerosol-forming substrate or may be a constituent part of a liquid aerosol-forming substrate, such as an aerosol former or a nicotine source. Where the first volatile liquid substrate is a constituent part of a liquid aerosol-forming substrate, the second volatile liquid substrate may be another constituent part of the aerosol-forming substrate and the combination of the first volatile substrate and the second volatile substrate may form the liquid aerosol-forming substrate.

The liquid aerosol-forming substrate may include water. In an embodiment, the liquid aerosol-forming substrate may also include an aerosol former such as propylene glycol or glycerine. The liquid aerosol-forming substrate may include a flavorant. The liquid aerosol-forming substrate may further include an active ingredient such as nicotine. In an embodiment, the liquid-aerosol-forming substrate may have a water content of between 10 and 25 weight percent, or for example between 12 and 20 weight percent. Water may be required to form a suitable inhalable aerosol. The liquid aerosol-forming substrate may include a nicotine solution. The liquid aerosol-forming substrate may include a tobacco-containing material including volatile tobacco flavor compounds which may be released from the liquid upon heating. The liquid aerosol-forming substrate may include a non-tobacco material. The liquid aerosol-forming substrate may include solvents, ethanol, plant extracts and natural or artificial flavors.

As used herein, the term "aerosol former" refers to any suitable known compound or mixture of compounds that, in use, facilitates formation of a dense and stable aerosol. An aerosol former may be substantially resistant to thermal degradation at the operating temperature of the aerosol-generating article. Suitable aerosol formers may be well-known in the art and may include, but are not limited to: polyhydric alcohols, such as triethylene glycol, 1,3-butane-diol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. In an embodiment, aerosol formers may be polyhydric alcohols or mixtures thereof, such as triethylene glycol, 1,3-butanediol and glycerine.

In an embodiment, in a heated aerosol-generating system, an airflow path may be defined when the heated aerosol-generating article may be coupled to the aerosol-generating device. The air flow path may include a point at which air enters the aerosol-generating device, a point at which air passes into the distal end of the heated aerosol-generating article, a point at which air passes over the liquid retention medium, and a point at which air passes out of the outlet end of the heated aerosol-generating article. In an embodiment, a system may include an aerosol-generating device acting to heat air at a point between entry into the aerosol-generating device and passing over the liquid retention medium. This may allow heated air to vaporize a liquid aerosol-forming substrate retained by the liquid retention medium. Heating of the air may be accomplished by a heater such as a heating coil that may be located within the airflow path, and may act to directly heat the air prior to that air passing over the liquid retention medium.

The heated aerosol-generating system may include an air permeable heat accumulator or heat diffuser that may be arranged in the air flow path to heat air. The term heat diffuser is defined below. The heat diffuser may interact with a heater and take on heat energy. The heat energy may then transfer to air that may pass through the heat diffuser. A heat diffuser may be an element having a high surface area and high porosity. Air may be able to flow through the heat diffuser without undergoing a significant pressure drop. Examples of suitable heat diffusers may be a porous metallic foam or a porous ceramic foam element arranged both in thermal contact with a heater and within the air flow path of the heated aerosol-generating system.

A heat diffuser may be a removable element of a heated aerosol-generating system. For example, heat diffuser may be in the form of a removably couplable element that may engage with an aerosol generating device to alter the manner in which the aerosol generating device heats aerosol generating articles. As an example, an aerosol generating device may include an insertable heating element for insertion into a solid aerosol forming substrate of a heated aerosol-generating article. The heating element may contact the solid aerosol-forming substrate and heat it to generate an aerosol. A heat diffuser may be configured to engage with the insertable heating element. The heat diffuser may then be heated by the heating element and heat air that may pass through the heating element. The heated air may then volatilize an aerosol-forming substrate of a heated aerosol-generating article that may be located downstream of the heat diffuser. In this way, the manner in which the aerosol-generating device may heat an aerosol-forming substrate may be changed from direct contact to indirect heating of air. The same aerosol-generating device may then be used to heat different types of aerosol-generating article.

In an embodiment, a system may include a heated aerosol-generating device, at least one heated aerosol-generating article as described above that may have a liquid aerosol-forming substrate, and at least one heated aerosol-forming substrate that may have a solid aerosol-forming substrate, for example an aerosol-forming substrate made from homogenized tobacco material. In an embodiment, the system may further include a removably couplable heat diffuser for engagement with the aerosol-generating device to change the manner in which the aerosol-generating device may provide heat to the aerosol-forming substrate.

In an embodiment, the aerosol-generating device may be a portable or handheld aerosol-generating device that may be comfortable to hold between the fingers of a single hand.

The aerosol-generating device may be substantially cylindrical in shape. The aerosol-generating device may have a length of between approximately 70 millimetres and approximately 120 millimetres.

The device may include a power supply for supplying electrical power to the electric heating element. The power supply may be any suitable power supply, for example a DC voltage source such as a battery. In one embodiment, the power supply may be a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

The controller may be a simple switch. Alternatively, the controller may be electric circuitry and may include one or more microprocessors or microcontrollers.

In another embodiment, a heated aerosol-generating article may be used with an electrically-operated aerosol-generating device. The heated aerosol-generating article may be a consumable article having an outlet end, a distal end upstream from the outlet end, and a mid-point that may be located an equal distance between the outlet end and the distal end. The article may include: a liquid aerosol-forming substrate contained within a frangible capsule, where the frangible capsule may be located between the distal end and the mid-point, and a liquid retention medium, at least a portion of which may be located between the distal end and the mid-point, in which the article may be configured such that, during use, air may be drawn through the article from the distal end to the outlet end.

In an embodiment of the heated aerosol-generating article, one or more of the following features may be used:

the liquid aerosol-forming substrate may be releasably contained within the frangible capsule and the liquid retention medium may be located in proximity to the frangible capsule for retaining the liquid aerosol-forming substrate within the article after its release from the frangible capsule;

the heated aerosol-generating article may include a plurality of elements assembled by a wrapper in the form of a rod;

the frangible capsule may be located within the liquid retention medium in the heated aerosol-generating article;

the liquid retention medium may be in the form of a tube having a lumen and the frangible capsule may be located within the lumen of the tube;

the liquid retention structure may include an absorbent polymeric material;

the frangible capsule may be configured to be ruptured by application of external force;

the frangible capsule may be configured to be pierced by a piercing element;

the heated aerosol-generating article may include a cooling section located downstream from the liquid retention element;

the liquid aerosol-forming substrate may include between 10 weight percent and 25 weight percent water, an aerosol former, and at least one flavorant;

the heated aerosol-generating article may include a mouthpiece filter located at the outlet end of the article;

the heated aerosol-generating article may include a porous plug located at the distal end of the article;

In an embodiment of the heated aerosol-generating system, the system may include a heated aerosol-generating article according to the second aspect of the invention, and an electrically-operated aerosol-generating device, the electrically-operated aerosol-generating device including structure for heating the aerosol-forming substrate so as to form an aerosol. The heated aerosol-generating system may include a piercing element for piercing the frangible capsule.

A method of using a heated aerosol generating article may include the steps of: releasing the liquid aerosol-forming substrate from the frangible capsule such that it may be retained by the liquid retention medium; coupling the heated aerosol-generating article to an electrically-operated aerosol-generating device; activating a heating structure of the electrically-operated aerosol-generating device; and drawing air through the heated aerosol-generating article, the liquid aerosol-forming substrate being vaporized by heat energy supplied by the heating structure and condensing to form an aerosol entrained in the air. The heating structure may heat air that may be drawn into the heated aerosol-generating article, the heated air may pass over or through the liquid retention medium to allow formation of an aerosol. The heating structure may heat the liquid retention medium by conduction or radiation to allow formation of an aerosol.

In another embodiment, a heated aerosol-generating article may include a plurality of elements that may be coaxially aligned and assembled within a wrapper. The article may have an outlet end and a distal end upstream from the outlet end, and the article may include: a liquid aerosol-forming substrate, and a liquid retention medium that may retain the liquid aerosol-forming substrate, in which the wrapper may be formed from a sheet of liquid-impervious material.

In an embodiment of the heated aerosol-generating article, one or more of the following features may be used:

the liquid aerosol-forming substrate may be releasably contained within a frangible capsule, the frangible capsule may be located in proximity to the liquid retention medium for retaining the liquid aerosol-forming substrate within the article after its release from the frangible capsule;

the frangible capsule may be located within the liquid retention medium;

the liquid retention medium may be in the form of a tube having a lumen and the frangible capsule may be located within the lumen of the tube;

the liquid retention medium may include an absorbent polymeric material;

the frangible capsule may be configured to be ruptured by application of external force;

the frangible capsule may be configured to be pierced by a piercing element;

the heated aerosol-generating article may include a cooling section located downstream from the liquid retention element;

the liquid aerosol-forming substrate may include between 10 weight percent and 25 weight percent water, an aerosol former, and at least one flavorant;

the heated aerosol-generating article may include a mouthpiece filter located at the outlet end of the article;

the heated aerosol-generating article may include a plug located at the distal end of the article, the article being configured such that air may be drawn into the article at or adjacent to the distal end, through the article, and out of the outlet end of the article;

the wrapper may be a sheet of polymeric material, a sheet of treated paper, or a sheet of metallic foil.

In an embodiment of the heated aerosol-generating system, the system may include a heated aerosol-generating article according to another embodiment, and an electrically-operated aerosol-generating device, the electrically-operated aerosol-generating device including structure for heating the aerosol-forming substrate so as to form an aerosol.

A method of using a heated aerosol generating article according to another embodiment may include the steps of: coupling the heated aerosol-generating article to an electrically-operated aerosol-generating device; activating a heating structure of the electrically-operated aerosol-generating device; and drawing air through the heated aerosol-generating article, the liquid aerosol-forming substrate being vaporized by heat energy supplied by the heating structure and condensing to form an aerosol entrained in the air. The liquid aerosol-forming substrate may be contained within a frangible capsule, and the method may further include the step of releasing the liquid aerosol-forming substrate from the frangible capsule such that it may be retained within the article by the liquid retention medium.

In another embodiment, a heated aerosol-generating article for use with an electrically-operated aerosol-generating device may include a consumable article having an outlet end, a distal end upstream from the outlet end, and a mid-point located an equal distance between the outlet end and the distal end, where the article may include: a first volatile liquid substrate contained within a first frangible capsule, the frangible capsule being located between the distal end and the mid-point; a second volatile liquid substrate contained within a second frangible capsule, the second frangible capsule being located between the distal end and the mid-point; and a liquid retention medium, at least a portion of which may be located between the distal end and the mid-point, in which the article may be configured such that, during use, air may be drawn through the article from the distal end to the outlet end.

In some variants of the heated aerosol-generating article according to another embodiment, one or more of the following features may be used:

the article may include a liquid aerosol-forming substrate, the first volatile liquid substrate including a first constituent of the liquid aerosol-forming substrate and the second volatile liquid substrate including a second constituent of the liquid aerosol-forming substrate;

the liquid aerosol-forming substrate including between 10 weight percent and 25 weight percent water, an aerosol former, and at least one flavorant;

the first volatile liquid substrate including a first liquid aerosol-forming substrate and the second volatile substrate including a second liquid aerosol-forming substrate;

the first volatile liquid substrate may be releasably contained within the first frangible capsule and the liquid retention medium may be located in proximity to the first frangible capsule for retaining the first volatile liquid substrate within the article after it may be released from the first frangible capsule, and the second volatile liquid substrate may be releasably contained within the second frangible capsule and the liquid retention medium may be located in proximity to the second frangible capsule for retaining the second volatile liquid substrate within the article after it may be released from the second frangible capsule;

the heated aerosol-generating article may include a plurality of elements assembled by a wrapper in the form of a rod;

the first and second frangible capsules may be located within the liquid retention medium;

the liquid retention medium may be in the form of a tube having a lumen and the first and second frangible capsules may be located within the lumen of the tube;

the first and second frangible capsules may be coaxially aligned in the lumen of the tube;

the liquid retention medium may include an absorbent polymeric material;

at least one of the first and second frangible capsules may be configured to be ruptured by application of external force;

at least one of the first and second frangible capsules may be configured to be pierced by a piercing element;

the heated aerosol-generating article may include a cooling section located downstream from the liquid retention medium;

the heated aerosol-generating article may include a mouthpiece filter located at the outlet end of the article;

the heated aerosol-generating article may include a porous plug located at the distal end of the article.

In an embodiment of the heated aerosol-generating system, the system may include a heated aerosol-generating article as described above, and an electrically-operated aerosol-generating device, the electrically-operated aerosol-generating device including structure for heating at least one of the first volatile liquid substrate and the second volatile liquid substrate that may be retained in the liquid retention medium so as to form an aerosol. The heated aerosol-generating system may include a piercing element for piercing at least one of the frangible capsules.

According to another embodiment, an electrically operated aerosol-generating device and a heat diffuser may be configured for use with an aerosol-generating article. The aerosol-generating article may include an aerosol-forming substrate and may have an outlet end and a distal end upstream from the outlet end. The electrically operated aerosol-generating device may include an electric heating element and a housing having a cavity configured to receive the distal end of the aerosol-generating article. The heat diffuser may be removably couplable to the aerosol-generating device and may include a non-combustible porous body for absorbing heat from the electric heating element when the heat diffuser may be coupled to the aerosol-generating device such that, in use, air may be drawn through the aerosol-generating article from the distal end to the outlet end may be heated by the heat absorbed in the porous body.

According to another embodiment, an electrically operated aerosol-generating device for an aerosol-generating may include: a housing having a cavity that may be configured to receive the distal end of an aerosol-generating article; an electric heating element; and a heat diffuser including a non-combustible, air permeable main body for absorbing and storing heat from the electric heating element such that, in use, air may be drawn through the main body of the heat diffuser and may be heated by heat stored in the main body.

The articles described above may be used any combination of the systems described above.

Features described in relation to one or more aspects may equally be applied to other embodiments.

Structural Embodiments

FIG. 1 illustrates a longitudinal cross-section of a heat diffuser 100 of an aerosol-generating system, in accordance with an example embodiment. The heat diffuser 100 may include a porous body 110 that may be in the form of a cylindrical plug of thermally conductive material. The porous body 110 may have an upstream or distal end 120, and a downstream or proximal end 130, opposite to the upstream end 120. The body 110 may define a cavity that may be in the form of a slot 140 that may be in the upstream end 120 of the porous body 110, and may be arranged to receive a blade-shaped heating element, as discussed below in relation to FIG. 3. The pores in the porous body 110 may be interconnected to form a plurality of air flow passages extending through the porous body 110 from its upstream end 120 to its downstream end 130.

FIGS. 2A to 2H illustrate embodiments of an aerosol-generating article. The articles shown in FIGS. 2A-H may be used with the aerosol-generating devices described below, or with other aerosol-generating devices. The articles shown in FIGS. 2A-H may also be used with the aerosol-generating systems described below, or with other aerosol-generating systems.

Figure 2A:
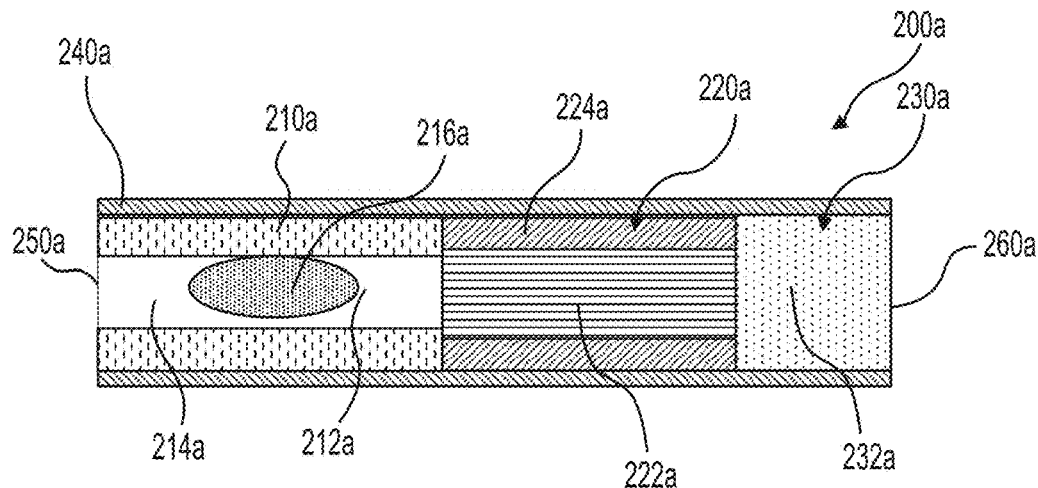
FIG. 2A illustrates a longitudinal cross-section of an aerosol-generating article that may be used with the heat diffuser of FIG. 1, in accordance with an example embodiment.

FIG. 2A illustrates a longitudinal cross-section of an aerosol-generating article 200a that may be used with the heat diffuser 100 of FIG. 1, in accordance with an example embodiment. An aerosol generating article may also be called a heated aerosol-generating article. The aerosol-generating article 200a may include three elements arranged in coaxial alignment: a tubular liquid retention medium 210a, an aerosol-cooling element 220a, and a mouthpiece 230a. The aerosol cooling element 220a may also be called an aerosol-generating section. The mouthpiece 230a may also be called a mouthpiece filter. Each of these three elements may be a substantially cylindrical element, with each having substantially the same diameter. These three elements may be arranged co-axially, and circumscribed by an outer wrapper 240a, to form a cylindrical rod. The outer wrapper 240a may be non-porous. The outer wrapper 240a may be liquid-impervious.

The aerosol-generating article 200a may have a distal or upstream end 250a, and a proximal or outlet end 260a, opposite to the upstream end 250a. Once assembled, the total length of the aerosol-generating article 200a may be about 33 mm about 45 mm, and the diameter may be about 7.2 mm.

The liquid retention medium 210a may be located at the extreme distal or upstream end 250a of the aerosol-generating article 200a. In an embodiment, the article 200a may include a frangible capsule 212a that may be located within the lumen 214a of the liquid retention medium 210a. The frangible capsule 212a may contain a liquid aerosol-forming substrate 216a.

The tubular liquid retention medium 210a may have a length of 8 mm, and may be formed from fibrous cellulose acetate material. The liquid retention medium 210a may have a capacity to absorb 35 microliters of liquid. The lumen 214a of the tubular liquid retention medium 210a may provide an air flow path through the liquid retention medium 210a, and also may act to position the frangible capsule 212a. The material of the liquid retention medium 210a may be any other suitable fibrous or porous material.

The frangible capsule 212a may be shaped as an oval spheroid, and may have a long dimension of the oval aligned with the axis of the lumen 214a. The oval spheroid shape of the capsule may mean that it may be easier to break, than if it was circular spherical in shape, but other shapes of capsule may also be used. The capsule 212a may have an outer shell including a gelatin based polymeric material, surrounding a liquid aerosol-forming substrate.

The liquid aerosol-forming substrate 216a may include propylene glycol, nicotine extract, and 20 weight percent water. A wide range of flavorants may be optionally added. A wide range of aerosol formers may be used as alternative, or in addition to, propylene glycol. The capsule 212a may be about 4 mm in length, and may contain a volume of about 33 microliters of liquid aerosol-forming substrate.

The aerosol-cooling section 220a may have a length of 18 mm. The aerosol-cooling section 220a may include a crimped and gathered sheet of polymeric material 222a. The sheet of polymeric material 222a may not be densely packed, and therefore the aerosol-cooling section 220a may not cause significant pressure drop in air passing through the section 220a. The crimped and gathered sheet of polymeric material 222a may be termed an aerosol-cooling element, and may have a length of about 18 mm, an outer diameter of about 7.12 mm, and an inner diameter of about 6.9 mm. In one embodiment, the aerosol-cooling element 220a may be formed from a sheet of polylactic acid having a thickness of 50 mm±2 mm. The sheet of polylactic acid may be crimped and gathered to define a plurality of channels that may extend along a length of the aerosol-cooling element 220a. A total surface area of the aerosol-cooling element 220a may be between 8000 $mm^2$ and 9000 $mm^2$, which may be equivalent to approximately 500 $mm^2$ per mm length of the aerosol-cooling element 220a. The specific surface area of the aerosol-cooling element 222a may be approximately 2.5 $mm^2$/mg and it may have a porosity of between 60% and 90% in the longitudinal direction. The polylactic acid may be kept at a temperature of 160 degrees Celsius or less during use.

Porosity may be defined herein as a measure of unfilled space in a rod including material such as an aerosol-cooling element 222a. For example, if a diameter of the rod was 50% unfilled by the aerosol-cooling element 222a, the porosity would be 50%. Likewise, a rod would have a porosity of 100%, if the inner diameter was completely unfilled, and a porosity of 0% if completely filled. The porosity may be calculated using known methods.

The aerosol-cooling element 220a may be located immediately downstream of the liquid retention medium 210a, where the aerosol-cooling element 220a may directly abut the liquid retention medium 210a. In use, volatile substances released from the aerosol-forming substrate 216a may pass along the aerosol-cooling element 220a, towards the outlet end 260a of the aerosol-generating article 200a. The volatile substances may be cooled within the aerosol-cooling element 220a, to form an aerosol. In an embodiment, the aerosol-cooling element 220a may include a crimped and gathered sheet 222a of polylactic acid circumscribed by a wrapper 224a. The crimped and gathered sheet 222a of polylactic acid may define a plurality of longitudinal channels that may extend along a length of the aerosol-cooling element 220a.

In an alternative embodiment, the aerosol-cooling section 220a may be a hollow section, such as a hollow tube, and may not include an aerosol-cooling element 220a. Such an embodiment is described below.

The mouthpiece 230a may be located immediately downstream of the aerosol-cooling element 220a, where the mouthpiece 230a may directly abut the aerosol-cooling element 220a. In an embodiment, the mouthpiece 230a may include a cellulose acetate tow filter 232a of low filtration efficiency. The mouthpiece filter 230a may have a length of 7 mm and may be formed from cellulose acetate tow. Other suitable mouthpiece filters that are well-known in the art may be used.

To assemble the aerosol-generating article 200a, the three cylindrical elements described above may be aligned and tightly wrapped within the outer wrapper 240a. In an embodiment, the outer wrapper 240a may be formed from a non-porous sheet material. The wrapper 240a may be a liquid-impervious wrapper, for example a wax-coated paper. Other suitable no-porous or liquid-impervious materials that are well-known may be used, such as for example polymeric films or hydrophobic papers. In an embodiment, the outer wrapper may include a porous material, such as cigarette paper.

Figure 2B:
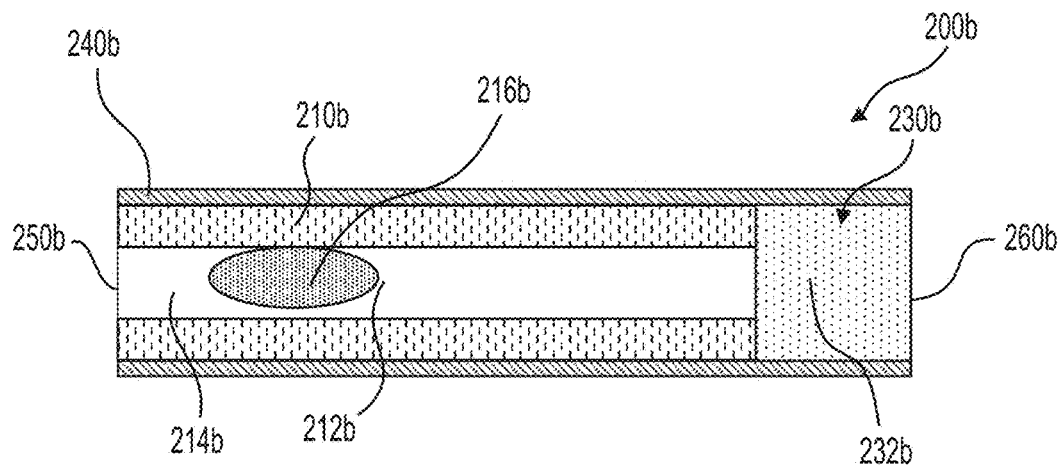
FIG. 2B illustrates a longitudinal cross-section of another aerosol-generating article that may be used with the heat diffuser of FIG. 1, in accordance with an example embodiment.
Figure 2C:
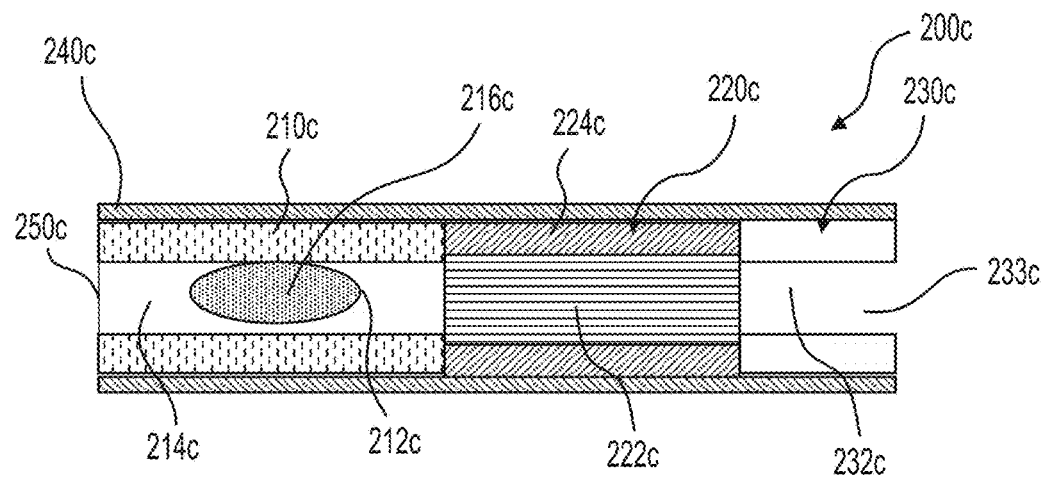
FIG. 2C illustrates a longitudinal cross-section of another aerosol-generating article that may be used with the heat diffuser of FIG. 1, in accordance with an example embodiment.
Figure 2D:
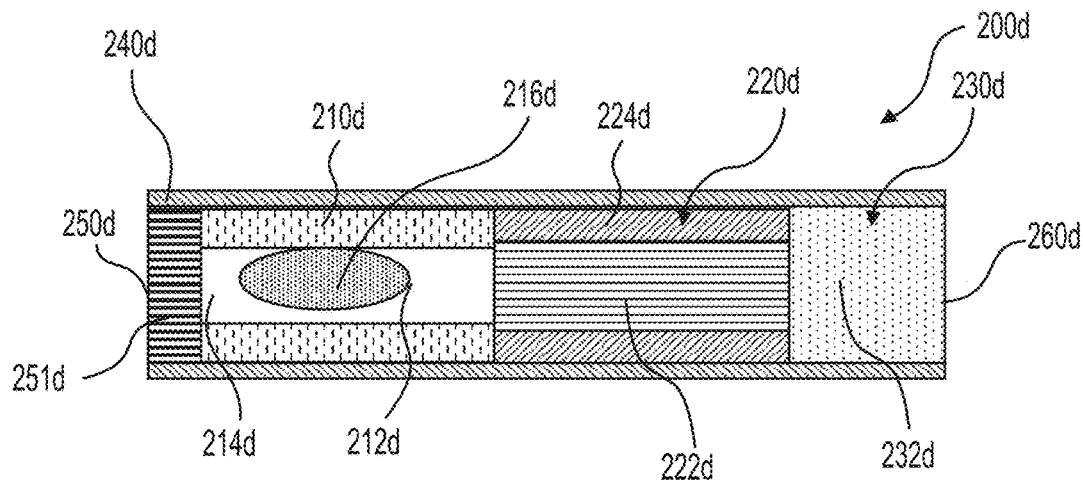
FIG. 2D illustrates a longitudinal cross-section of another aerosol-generating article that may be used with the heat diffuser of FIG. 1, in accordance with an example embodiment.

FIGS. 2B to 2D illustrate other embodiments of a heated aerosol-generating article.

FIG. 2B illustrates a heated aerosol-generating article 200b having a tubular liquid retention medium 210b and a mouthpiece filter 232b assembled in abutting relationship within a wrapper 240b. The article 200b may have a distal end 250b and an outlet end 260b. The wrapper 240b may be non-porous or liquid-impervious. The lumen 214b defined by the tubular liquid retention medium 210b may hold a frangible capsule 212b containing a liquid aerosol-forming substrate may be located within a lumen 214b of the liquid retention medium 210b. The overall length of the article 200b may be about 30 mm. The liquid retention medium 210b may have a length of 20 mm, and the filter 232b may have a length of 10 mm. The materials of the liquid retention medium 210b, the frangible capsule 212b, the liquid aerosol-forming substrate 216b, and the mouthpiece filter 232b of the mouthpiece 230b, may be the same as described above in relation to FIG. 2A.

FIG. 2C illustrates a heated aerosol-generating article 200c that may be similar to the article 200a of FIG. 2A, where like reference numbers are not described again here, for sake of brevity. However, article 200c may differ from article 200a from the standpoint that article 200c may have a rigid hollow mouthpiece 230c. The mouthpiece 230c may be tubular, and may define a lumen 233c that may define an air flow path 232c.

FIG. 2D illustrates a heated aerosol-generating article 200d that may be similar to the article 200a (FIG. 2A), where like reference numbers are not described again here, for sake of brevity. However, article 200d may differ from article 200a from the standpoint that article 200d may include a front-plug 251d that may be disposed at the distal end 250d of the article 200d. The front-plug 251d may have a length of 3 mm, and may span the distal end 250d of the article 200d. The front plug 251d may be formed of a highly porous cellulose acetate material, and may provide an air flow path into the article 200d. The front-plug 251d may help to prevent egress of the liquid aerosol-forming substrate 216d during use of the article 200d.

Figure 2E:
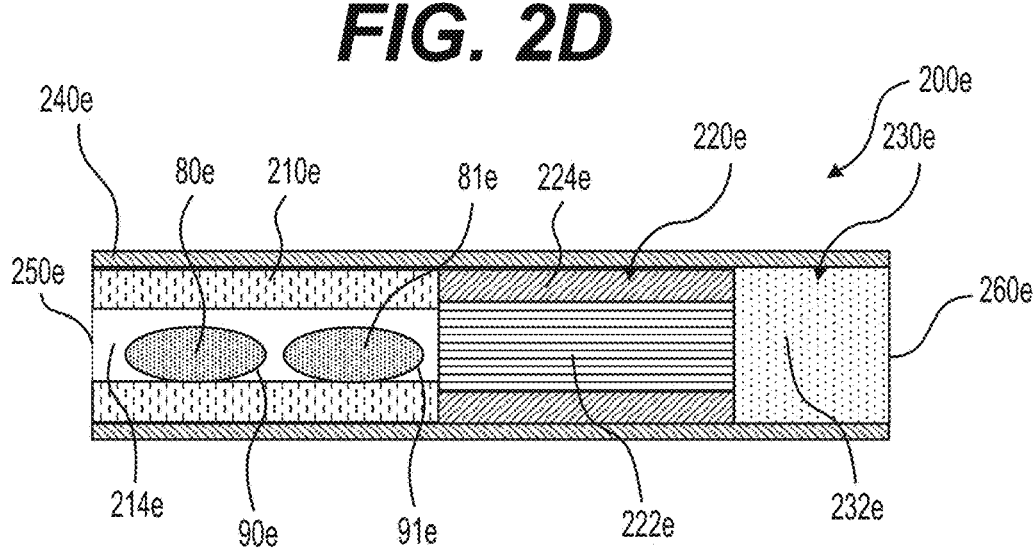
FIG. 2E illustrates a longitudinal cross-section of another aerosol-generating article that may be used with the heat diffuser of FIG. 1, in accordance with an example embodiment.

FIG. 2E illustrates an embodiment of a heated aerosol-generating article 200e that may be similar to the article 200a (FIG. 2A), where like reference numbers are not described again here, for sake of brevity. However, article 200e may differ from article 200a from the standpoint that article 200e may include a first volatile liquid substrate 80e that may be contained within a first frangible capsule 90e, and a second liquid volatile substrate 81e that may be contained within a second frangible capsule 91e. The first frangible capsule 90e may be located within a lumen 214e of the tubular liquid retention medium 210e. The second frangible capsule 91e may also be located within the lumen 214e of the tubular liquid retention medium 200e, and may be arranged co-axially with the first frangible capsule 91e within the lumen 214e, such that the first frangible capsule 90e may be arranged towards the distal end 250e and the second frangible capsule 91e may be arranged towards the aerosol-generating section 220e (closer to the outlet end 260e).

The first frangible capsule 90e may be shaped as an oval spheroid, and may have the long dimension of the oval aligned with the axis of the lumen 214e. The oval spheroid shape of the first frangible capsule 90e may mean that it may be easier to break than if it was circular spherical in shape, but other shapes of capsule may also be used. The first frangible capsule 90e may have an outer shell including a gelatin based polymeric material surrounding the liquid aerosol-forming substrate 80e.

The second frangible capsule 91e may be identical to the first frangible capsule 90e. The second frangible capsule 91e may also be of different material or shape than the first frangible capsule 90e. The first frangible capsule 90e, or the second frangible capsule 91e, or both, may have a different shape, or a different construction, from that described above.

The first volatile liquid substrate 80e may include propylene glycol, nicotine extract, and 20 weight percent water. A wide range of flavorants may be optionally added. A wide range of aerosol-formers may be used as alternative, or in addition to, propylene glycol. The capsule 90e may have a long axis that may be about 4 mm in length, and may contain a volume of about 33 microliters of the first liquid aerosol-forming substrate 80e.

The second volatile liquid substrate 81e also may include propylene glycol, nicotine extract, and 20 weight percent water, but may include a different flavorant, as compared to the first volatile liquid substrate 80e. The second frangible capsule 91e may have a long axis that may be about 4 mm in length, and may contain a volume of about 33 microliters of the second liquid aerosol-forming substrate 81e.

Figure 2F:
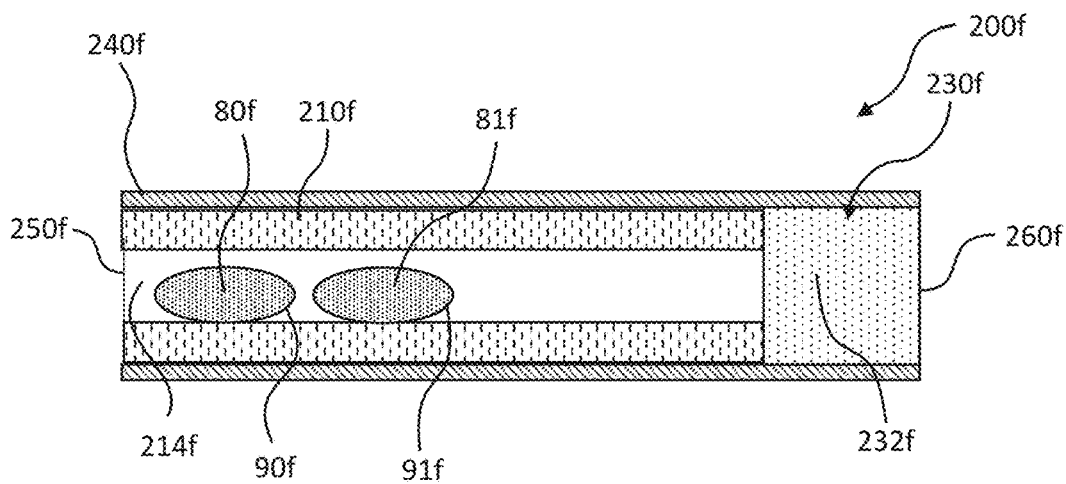
FIG. 2F illustrates a longitudinal cross-section of another aerosol-generating article that may be used with the heat diffuser of FIG. 1, in accordance with an example embodiment.

FIG. 2F illustrates a heated aerosol-generating article 200f having a tubular liquid retention medium 210f and a mouthpiece filter 232f assembled in abutting relationship within a non-porous wrapper 240f. A first frangible capsule 90f that may contain a liquid aerosol-forming substrate 80f may be located within a lumen 214f of the liquid retention medium 210f. A second frangible capsule 91f that may contain the liquid aerosol-forming substrate 81f may also be located within the lumen 214f of the liquid retention medium 210f. The overall length of the article 200f may be about 30 mm. The liquid retention medium 210f may have a length of 20 mm, and the filter 232f may have a length of about 10 mm. The materials of the liquid retention medium 210f, the first and second frangible capsules 90f/91f, and the mouthpiece filter 232f, may be the same as described above in relation to FIGS. 2A and 2E. The liquid aerosol-forming substrate 80f/81f may include propylene glycol, nicotine extract, 20 weight percent water and various flavorants.

Figure 2G:
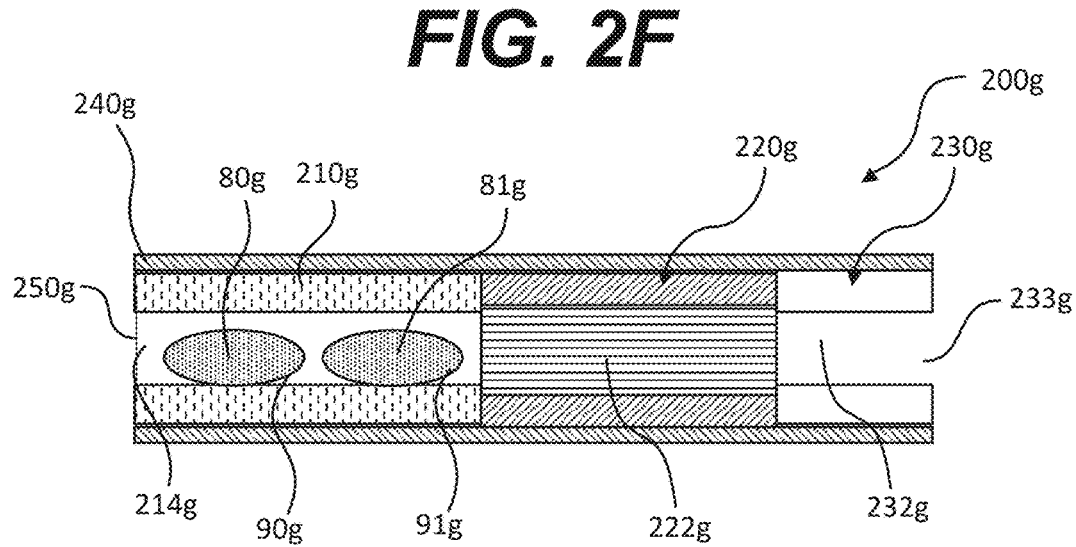
FIG. 2G illustrates a longitudinal cross-section of another aerosol-generating article that may be used with the heat diffuser of FIG. 1, in accordance with an example embodiment.

FIG. 2G illustrates a heated aerosol-generating article 200g that may be similar to the article 200e (FIG. 2E), where like reference numbers are not described again here, for sake of brevity. However, article 200g may differ from article 200e from the standpoint that article 200g may include a rigid hollow mouthpiece 230g. The mouthpiece 230g may be tubular, and may define a lumen 233g that may define an air flow path 232g.

Figure 2H:
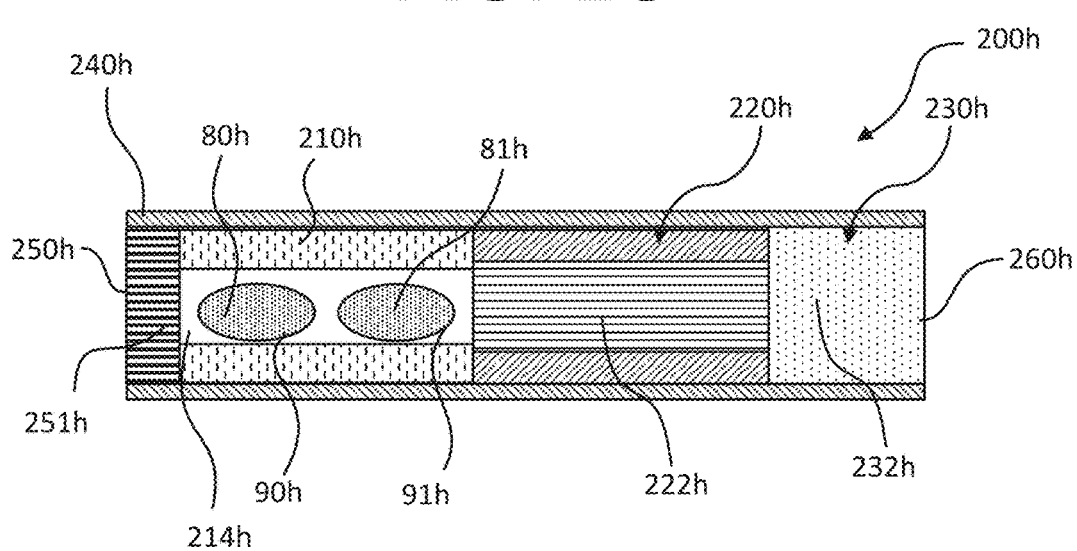
FIG. 2H illustrates a longitudinal cross-section of another aerosol-generating article that may be used with the heat diffuser of FIG. 1, in accordance with an example embodiment.

FIG. 2H illustrates a heated aerosol-generating article 200h that may be similar to article 200e (FIG. 2E), where like reference numbers are not described again here, for sake of brevity. However, article 200h may differ from article 200e from the standpoint that article 200h may include a front-plug 251h that may be disposed at a distal end 251h of the article 200h. The front-plug 251h may have a length of 3 mm, and may span the distal end 250h of the article 200h. The front plug 251h may be formed of a highly porous cellulose acetate material, and may provide an air flow path into the article 200h. The front-plug 251h may help to prevent egress of liquid aerosol-forming substrate 80h during use of the article 200h.

Figure 3:
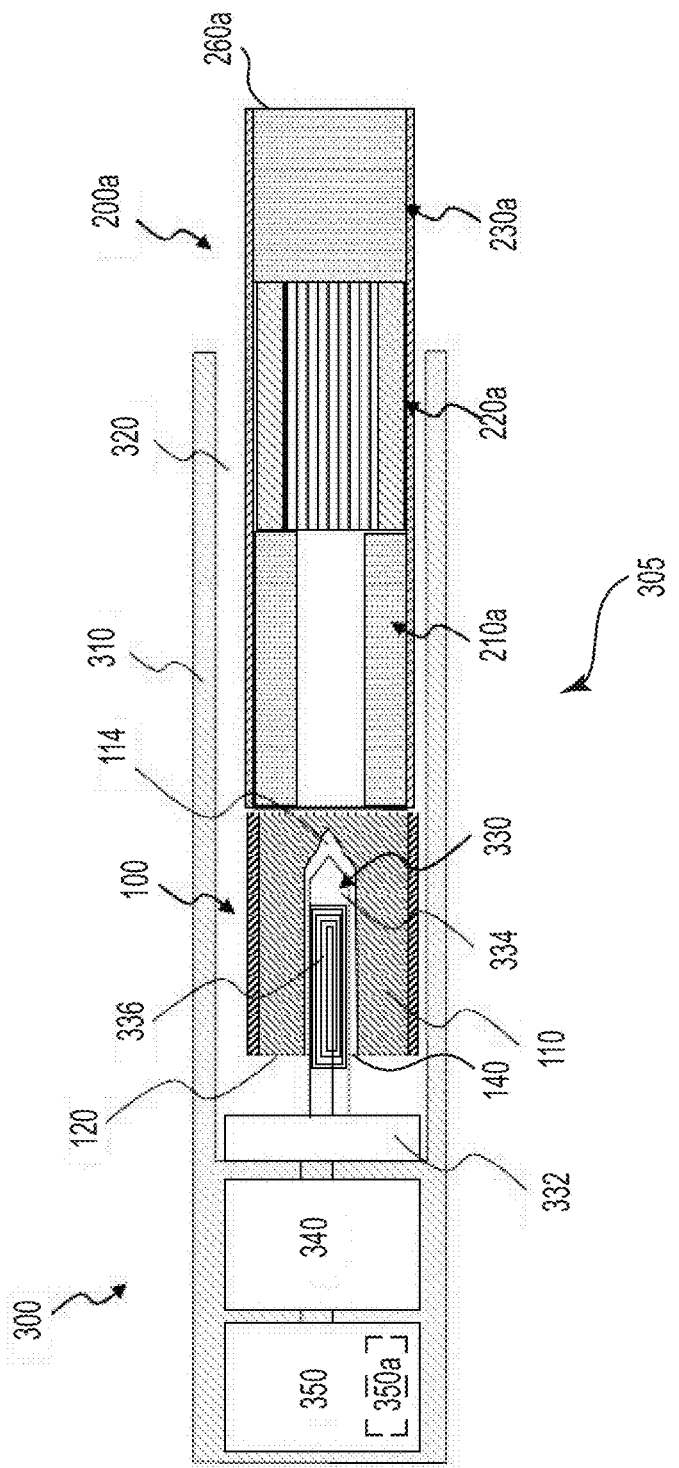
FIG. 3 illustrates the heat diffuser of FIG. 1, and the aerosol-generating article of FIG. 2A, connected to an aerosol-generating device, in accordance with an example embodiment.

FIG. 3 illustrates an aerosol-generating system 305, in accordance with an example embodiment. The aerosol-generating system 305 may include the heat diffuser 100, the aerosol-generating article 200a, and an aerosol-generating device 300. In an embodiment, the aerosol generating system 305 may instead include any of the aerosol-generating articles 200b-h described above. The system 305 will now be described in connection with the aerosol-generating article 200a. This description may apply equally to the other aerosol-generating article 200b-h embodiments.

The aerosol-generating device 300 may include a housing 310 that may define a cavity 320 that may receive the heat diffuser 100 and the aerosol-generating article 200a. The device 300 may further include a heater 330 that may include a base portion 332 and a heating element 334 that may be in the form of a heater blade that may penetrate the heat diffuser 100, so that a portion of the heater blade 334 may extend into the slot 140 in the porous body 110 when the heat diffuser 100 may be received in the cavity 320. The heater blade 334 may include resistive heating tracks 336 that may resistively heat the heat diffuser 100. A controller 340 may include circuitry that controls the operation of the device 300, including the supply of electrical current from a power source 350, such as a battery, to the resistive heating tracks 336 of the heater blade 334.

As depicted in FIG. 3, the frangible capsule 212a (FIG. 2A) may already have been ruptured, prior to insertion of the article 200a into the cavity 320 of the device 300, which FIG. 3 illustrates. Thus, the liquid aerosol-forming substrate 216a is depicted as being already absorbed into the liquid retention medium 210a. In an embodiment, the frangible capsule 212a may be ruptured following, or during, insertion of the aerosol-generating article 200a into the cavity 320 of the device 300. For example, the heat diffuser 100 may have a piercing member at its downstream end which may be arranged to engage with and rupture the frangible capsule 212a during insertion of the aerosol-generating article 200a into the cavity 320.

During use, the controller 340 may supply electrical current from the battery 350 to the resistive heating tracks 336 to heat the heater blade 334. Thermal energy may then be absorbed by the porous body 110 of the heat diffuser 100 to heat the porous body 110. Air may be drawn into the device 300 through air inlets (not shown), and the air may subsequently be drawn through the heat diffuser 100 and along the aerosol-generating article 200a from the distal end 120 of the heat diffuser 100 to the outlet end 260a of the aerosol-generating article 200a. As air is drawn through the porous body 110, the air may be heated by the heat absorbed by the porous body 110 from the heater blade 334, before passing through the liquid retention medium 210a of the aerosol-generating article 200a to heat the liquid aerosol-forming substrate 216a in the liquid retention medium 210a. In the event the controller 340 is a processor executing software, the processor is configured as a special purpose machine to execute the software, stored in a storage medium (e.g., a memory 350a), to perform the functions of the controller 340. In such an embodiment, the processor may include one or more Central Processing Units (CPUs), digital signal processors (DSPs), application-specific-integrated-circuits (ASICs), field programmable gate arrays (FPGAs) computers.

During a heating cycle, at least some of the one or more volatile compounds within the aerosol-generating substrate 216a may evaporate. The vaporized aerosol-forming substrate may become entrained in the air flowing through the liquid retention medium 210a, and condense within the aerosol-cooling element 220a and the mouthpiece portion 230a of the system 305 in order to form a generated aerosol, where the aerosol may exit the aerosol-generating article 200a at the outlet end 260a.

Figure 4:
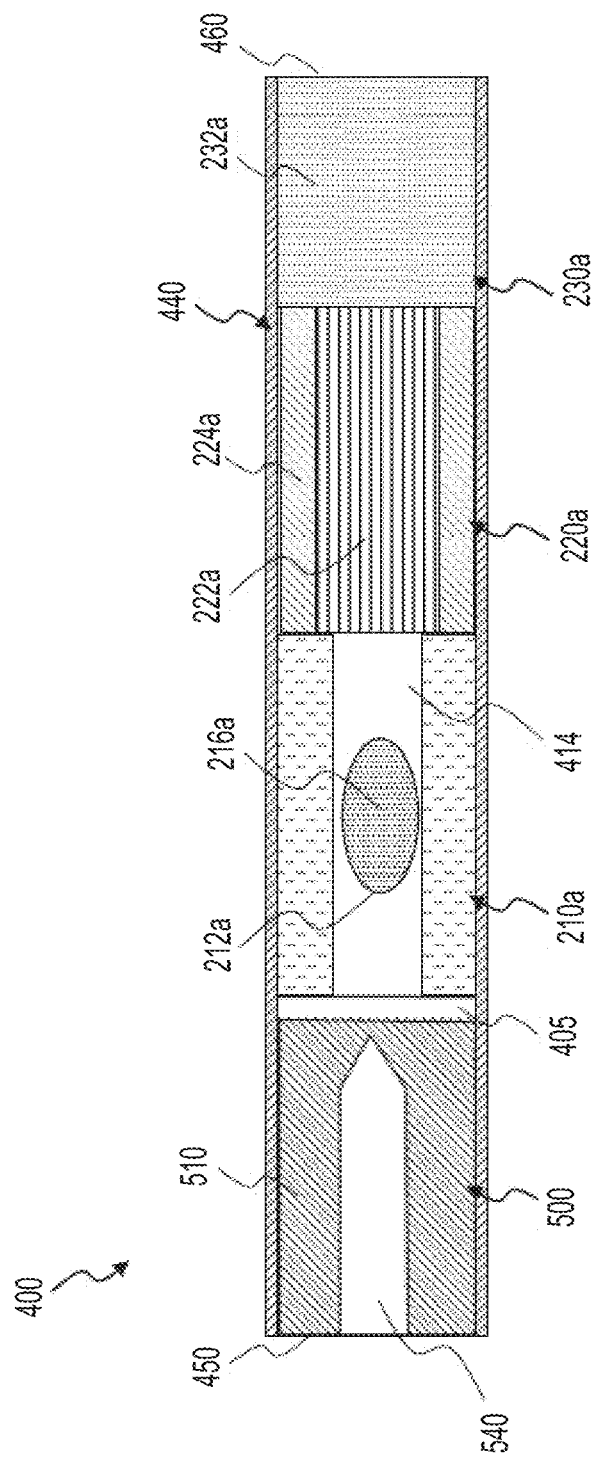
FIG. 4 illustrates a longitudinal cross-section of an aerosol-generating article with a heat diffuser, in accordance with an example embodiment.

FIG. 4 illustrates an aerosol-generating article 400 in accordance with an embodiment. The aerosol-generating article 400 may have similar structure to the aerosol-generating article 200a of FIG. 2A, where the same features are represented using like reference numerals which are generally not separately described here for sake of brevity. As with the aerosol-generating article 200a of FIG. 2A, the aerosol-generating article 400 may include a liquid retention medium 210a, an aerosol-cooling element 220a, and a mouthpiece 230a that may be arranged in coaxial alignment and circumscribed by a non-porous outer wrapper 440 to form a cylindrical rod. However, unlike the aerosol-generating article 200a of FIG. 2A, the aerosol-generating article 400 may include a heat diffuser 500 at the upstream end 450 of the aerosol-generating article 400. The heat diffuser 500 may include a porous body 510 that may be in the form of a cylindrical plug of heat storage material, such as ceramic foam. The heat diffuser 500 may also be circumscribed by the outer wrapper 440, such that the heat diffuser 500 may form part of the aerosol-generating article 400. A separation 405 may be provided between the downstream end of the heat diffuser 500 and the upstream end of the liquid retention medium 210a to minimize an extent to which the liquid retention medium 210a may be heated by conduction from the heat diffuser 500.

As the heat diffuser 500 may form part of the aerosol-generating article 400, the heat diffuser 500 may be removably coupled to a device (such as device 300 of FIG. 3), as an integral part of the aerosol-generating article 400, rather than as two separate elements (as shown in the embodiments of FIGS. 1-3). Use of the aerosol-generating article 400 may otherwise the same as discussed above, in relation to FIG. 3.

The heat diffuser 500 may also be combined with any of the embodiments of the aerosol-generating articles shown on FIGS. 2B-H, just as it has been shown combined with the aerosol-generating article 200a of FIG. 2A.

Although the embodiments shown in FIGS. 1-4 illustrate that the aerosol-generating articles 200a-h/400 may include one or more frangible capsules, in an embodiment, three or more frangible capsules may also be provided. In an embodiment, the articles 200a-h/400 may include a solid aerosol-forming substrate (such as the substrate 216a of FIG. 2A), in addition to, or instead of, the frangible capsules.

Furthermore, although the embodiments of FIGS. 1-4 illustrate a heating element 334 that may be a heating blade arranged to extend into the slot 140/540 of a heat diffuser 100/500, the heating element may be provided as one or more heating elements extending around the periphery of the cavity. Additionally or alternatively, the heating element 334 may be a susceptor located within the heat diffuser. For example, a blade-shaped susceptor may be located within the heat diffuser, in contact with a porous body. One or both ends of the susceptor may be sharpened or pointed to facilitate insertion into the heat diffuser.

Methods of using a heated aerosol-generating article according to example embodiments using the aerosol-generating articles shown in FIGS. 2A-D will be described with relation to the embodiment of FIG. 2A, for sake of brevity. It should be understood that the heated aerosol-generating articles disclosed herein are intended to be consumable items that may be engaged with a separate aerosol-generating device for consumption.

In an example embodiment, a first step of a method of use may be to release the liquid aerosol-forming substrate 216a from its frangible capsule 212a. This may be achieved by squeezing the article 200a in the region of the capsule 212a to apply an external force that may rupture the frangible capsule 212a. Once ruptured, the liquid aerosol-forming substrate 216a may be released onto and rapidly absorbed by the liquid retention medium 210a. The article 200a may thus be primed and ready for engagement with an aerosol-generating device.

Methods of using a heated aerosol-generating article according to example embodiments using the aerosol-generating article shown in FIGS. 2E-H will be described with relation to the embodiment of FIG. 2E, for sake of brevity. The heated aerosol-generating articles disclosed herein are intended to be consumable items that may be engaged with a separate aerosol-generating device for consumption.

In an example embodiment, a first step may be to release the first volatile liquid substrate 80e from the first frangible capsule 90e. This may be achieved by squeezing the article 200e in the region of the first frangible 90e capsule to apply an external force to rupture the first frangible capsule 90e. Once ruptured, the first liquid volatile substrate 80e may be released onto and rapidly absorbed by the liquid retention medium 210e.

Where the first liquid volatile substrate 80e is a first liquid aerosol-forming substrate, the article 200e may thus be primed and ready for engagement with an aerosol-generating device. After a first use of the aerosol-generating article 200e, the second liquid volatile substrate 81e may be released from the second capsule 91e by squeezing the article in the region of the second capsule 91e. The article 200e may thus be primed and ready for engagement with an aerosol-generating device again for a second use of the article.

Where the first liquid volatile substrate 80e is a constituent of a liquid aerosol-forming substrate, and the second liquid volatile substrate 81e is another constituent of the liquid aerosol-forming substrate, the second volatile liquid substrate 81e may also be released from the second frangible capsule 91e before the article 200e may be primed and ready for engagement with an aerosol-generating device. Releasing the second volatile liquid substrate 81e from the second frangible capsule 91e may cause the second volatile liquid substrate 81e to mix with the first volatile liquid substrate 80e in the liquid retention medium to form the liquid aerosol-forming substrate. This may be achieved by squeezing the article in the region of the second frangible capsule 91e to apply an external force to rupture the second frangible capsule 91e. Once ruptured, the second liquid volatile substrate 81e may be released onto and rapidly absorbed by the liquid retention medium, where it may mix with the first liquid volatile substrate 80e to form the liquid aerosol-forming substrate.

Figure 5:
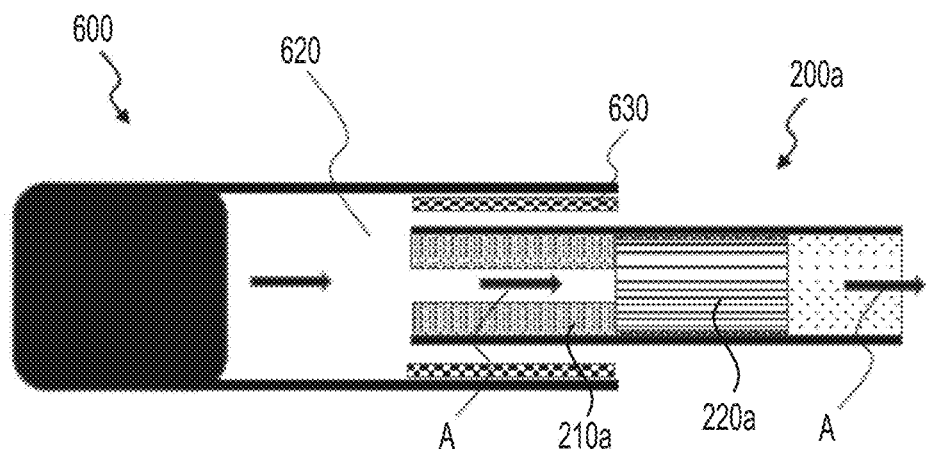
FIG. 5 illustrates an aerosol-generating article, during use, engaged with an aerosol-generating device that includes external heating elements, in accordance with an example embodiment.

FIG. 5 illustrates a use of an aerosol-generating device 600 having external heating elements 630. This description entails use of the device 600 with the aerosol-generating article 200a of FIG. 2A, for sake of brevity. However, this description applies equally to the embodiments of FIGS. 2B-H. The device 600 may define a cavity 620 for receiving a distal portion of the heated aerosol-generating article 200a. A plurality of external heating elements 630 may be located in the cavity 620 and, when the article 200a may be engaged within the cavity 620, the heating elements 630 may surround the liquid retention medium 210a. The external heating elements 630 may be activated in order to heat the liquid retention medium 210a by conduction. The external heating elements 630 may be activated to also heat the liquid retention medium 210a via radiation. The liquid aerosol-forming substrate 216a that may be retained within the liquid retention medium 210a may be heated and vaporized. As air is drawn through the article 200a, the vaporized aerosol-forming substrate 216a may be entrained in the air (shown by air flow path 'A'), as the air is drawn into the cooling element 220a of the article 200a. The vaporized aerosol-forming substrate 216a may cool within the aerosol-cooling section 220a and condense to form a generated aerosol. The generated aerosol may then be discharged from the vapor-generating article 200a.

Figure 6:
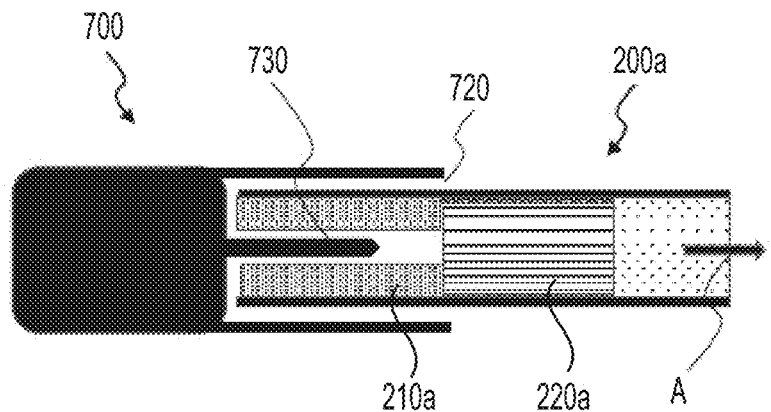
FIG. 6 illustrates an aerosol-generating article, during use, engaged with an aerosol-generating device that includes an internal heating element, in accordance with an example embodiment.

FIG. 6 illustrates the use of an aerosol-generating device 700 having an internal heating element 730. The aerosol-generating device 700 may include a solid aerosol-forming substrate 216a (not explicitly depicted in FIG. 6, as the frangible capsule 212a has already been ruptured, in this configuration). The device 700 may define a cavity 720 that may receive a distal portion 250a (FIG. 2A) of the heated aerosol-generating article 200a. A heating element 730, that may for example be blade-shaped, may be located in the cavity 720 and, when the article 200a may be engaged within the cavity 720 the heating element 730 may extend into the lumen 214a (FIG. 2A) of the liquid retention medium 210a. The internal heating element 730 may be activated to heat the liquid retention medium 210a by radiation. The liquid aerosol-forming substrate 216a may be retained within the liquid retention medium 210a to be heated and vaporized. Air may be drawn through the article 200a, such that the vaporized aerosol-forming substrate 216a may be entrained in the air that may be drawn through the cooling element 220a of the article 200a. The vaporized aerosol-forming substrate 216a may cool within the aerosol-cooling section 220a and condense to form a generated aerosol. The generated aerosol may be discharged from the article 200a. While the device 700 is shown interfacing with article 200a, it should be understood that the device 700 may also interface with any of the articles 200b-h described above.

Figure 7:
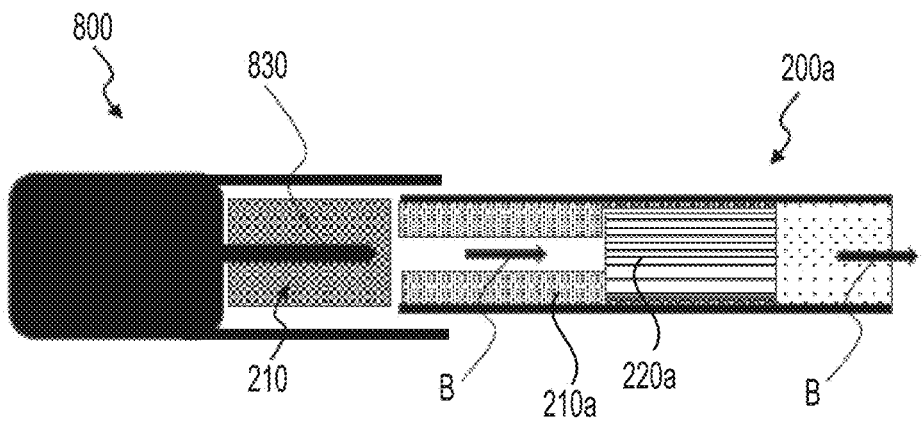
FIG. 7 illustrates an aerosol-generating article, during use, engaged with an aerosol-generating device that includes an internal heating element and a removably coupled heat diffuser, in accordance with an example embodiment.

FIG. 7 illustrates a use of the heated aerosol-generating article 200a. The aerosol-generating device 800 may be an aerosol-generating device having an internal heating element 830 (which may be identical to the heating element 730 of FIG. 6). The aerosol-generating device 800 may engage with a heat diffuser element 100 (FIG. 1), in addition to the aerosol-generating article 200a. The heat diffuser element 100 may be a substantially cylindrical element that may be formed from glass fibre. In an embodiment, the heat diffuser element 100 may be made from other porous materials, such as ceramic fibres, ceramic foams, or sintered metals. The heat diffuser element 100 may define one or more longitudinally extending slots 140 (FIG. 1) that may allow the heat diffuser element 100 to be penetrated by the heating element 830 of the aerosol-generating device 800. The internal heating element 830 may be activated to heat the heat diffuser element 100 by conduction. The internal heating element 830 may be activated to also heat the heat diffuser element 100 by radiation. Air may be drawn through the device 800 (see air flow 'B'), and the air may pass through the heat diffuser 100. The heated air may then be drawn into the aerosol-generating article 200a to pass through the liquid retention medium 210a. The liquid aerosol-forming substrate 216a may be retained within the liquid retention medium 210a (where the substrate 216a is not shown in FIG. 7, as the capsule 212a has already been ruptured in this configuration), and the substrate 216a may be heated and vaporized by this heated air. The air may be drawn through the article 200a, so that the vaporized aerosol-forming substrate 216a may be entrained in the air drawn through the cooling element 220a of the article 200a. The vaporized aerosol-forming substrate 216a may cool within the aerosol-cooling element 220a and condense to form a generated aerosol. The generated aerosol may then be discharged from the article 200a. While the device 800 is shown interfacing with article 200a, it should be understood that the device 800 may also interface with any of the articles 200b-h described above.

The specific embodiments and examples described above illustrate but do not limit the example embodiments. It is to be understood that other embodiments may be made, and the specific embodiments and examples described herein are not exhaustive.

What is claimed is:

1. An aerosol-generating article, comprising:
   a plurality of elements coaxially aligned and assembled within a wrapper, the aerosol-generating article having an outlet end and a distal end upstream from the outlet end;
   a liquid aerosol-forming substrate, the liquid aerosol-forming substrate being releasably contained within at least one frangible capsule; and
   a liquid retention medium being configured to retain the liquid aerosol-forming substrate within the aerosol-generating article after the release of the liquid aerosol-forming substrate from the at least one frangible capsule, the liquid retention medium being devoid of the liquid aerosol-forming substrate prior to the release of the liquid aerosol-forming substrate from the at least one frangible capsule, the wrapper being formed from a sheet of liquid-impervious material, the liquid retention medium being in a first element of the plurality of elements, and the liquid retention medium being positioned on the distal end.

2. The aerosol-generating article of claim 1, wherein the at least one frangible capsule is in the liquid retention medium.

3. The aerosol-generating article of claim 1, wherein the liquid retention medium is in the form of a tube having a lumen, and the at least one frangible capsule is located within the lumen of the tube.

4. The aerosol-generating article of claim 1, wherein the liquid retention medium includes an absorbent polymeric material.

5. The aerosol-generating article of claim 1, wherein the at least one frangible capsule is configured to rupture by application of an external force.

6. The aerosol-generating article of claim 1, wherein the at least one frangible capsule is configured to be pierced by a piercing element.

7. The aerosol-generating article of claim 1, further comprising:
a cooling section located downstream from the liquid retention medium, the cooling section being a second element of the plurality of elements.

8. The aerosol-generating article of claim 1, wherein the liquid aerosol-forming substrate includes between 10 weight percent and 25 weight percent water, an aerosol former, and at least one flavorant.

9. The aerosol-generating article of claim 1, further comprising:
a mouthpiece filter located at the outlet end of the aerosol-generating article, the mouthpiece filter being a third element of the plurality of elements.

10. The aerosol-generating article of claim 1, further comprising:
a plug located at the distal end, the aerosol-generating article being configured to draw air into the aerosol-generating article at or adjacent to the distal end, through the aerosol-generating article, and out of the outlet end if a negative pressure is applied at the outlet end.

11. The aerosol-generating article of claim 1, wherein the wrapper is one of a sheet of polymeric material, a sheet of treated paper, and a sheet of metallic foil.

12. The aerosol-generating article of claim 3, wherein the at least one frangible capsule is in the liquid retention medium.

13. The aerosol-generating article of claim 12, wherein the liquid retention medium includes an absorbent polymeric material.

14. The aerosol-generating article of claim 13, wherein the at least one frangible capsule is configured to be pierced by a piercing element.

15. The aerosol-generating article of claim 1, wherein the at least one frangible capsule includes a first frangible capsule and a second frangible capsule,
the first frangible capsule includes a first volatile liquid substrate,
the second frangible capsule includes a second volatile liquid substrate, the first volatile liquid substrate and the second volatile liquid substrate being the liquid aerosol-forming substrate, and
the first volatile liquid substrate includes a first constituent of the liquid aerosol-forming substrate and the second volatile liquid substrate includes a second constituent of the liquid aerosol-forming liquid aerosol generating substrate.

16. An aerosol-generating system, comprising:
an aerosol-generating article, the aerosol-generating article including,
a plurality of elements coaxially aligned and assembled within a wrapper, the aerosol-generating article having an outlet end and a distal end upstream from the outlet end,
a liquid aerosol-forming substrate, the liquid aerosol-forming substrate being releasably contained within at least one frangible capsule, and
a liquid retention medium being configured to retain the liquid aerosol-forming substrate within the aerosol-generating system after the release of the liquid aerosol-forming substrate from the at least one frangible capsule, the liquid retention medium being devoid of the liquid aerosol-forming substrate prior to the release of the liquid aerosol-forming substrate from the at least one frangible capsule, the wrapper being formed from a sheet of liquid-impervious material, the liquid retention medium being in a first element of the plurality of elements, the liquid retention medium being positioned on the distal end; and
an electrically-operated aerosol-generating device, the electrically-operated aerosol-generating device including a heating element for heating the liquid aerosol-forming substrate to form an aerosol.

17. The aerosol-generating system of claim 16, wherein the at least one frangible capsule is in the liquid retention medium.

18. A method of using an aerosol-generating article, the aerosol-generating article including a plurality of elements coaxially aligned and assembled within a wrapper, the aerosol-generating article having an outlet end and a distal end upstream from the outlet end, a liquid aerosol-forming substrate being releasably contained within at least one frangible capsule, and a liquid retention medium, the liquid retention medium being configured to retain the liquid aerosol-forming substrate within the aerosol-generating article after the release of the liquid aerosol-forming substrate from the at least one frangible capsule, the liquid retention medium being devoid of the liquid aerosol-forming substrate prior to the release of the liquid aerosol-forming substrate from the at least one frangible capsule, the wrapper being formed from a sheet of liquid-impervious material, the liquid retention medium being in a first element of the plurality of elements, and the liquid retention medium being positioned on the distal end, the method comprising:
coupling the aerosol-generating article to an electrically-operated aerosol-generating device;
activating a heating element of the electrically-operated aerosol-generating device; and
drawing air through the aerosol-generating article, the liquid aerosol-forming substrate being vaporized by heat energy supplied by the heating element and condensed to form an aerosol entrained in the air.

19. The method of claim 18, further including,
releasing the liquid aerosol-forming substrate from the frangible capsule such that it is retained within the aerosol-generating article by the liquid retention medium.

20. The method of claim 18, wherein the at least one frangible capsule is in the liquid retention medium.

* * * * *